(12) United States Patent
Blott et al.

(10) Patent No.: US 10,426,875 B2
(45) Date of Patent: Oct. 1, 2019

(54) WOUND CLEANSING APPARATUS IN-SITU

(71) Applicant: Smith & Nephew PLC, Watford, Hertfordshire (GB)

(72) Inventors: Patrick Lewis Blott, York (GB); Bryan Greener, York (GB); Edward Yerbury Hartwell, Hull (GB); Derek Nicolini, Hull (GB); Tina Michelle Walker, York (GB); Julian Lee-Webb, York (GB)

(73) Assignee: Smith & Nephew PLC, Watford (GB)

( * ) Notice: Subject to any disclaimer, the term of this patent is extended or adjusted under 35 U.S.C. 154(b) by 0 days.

(21) Appl. No.: 15/600,651

(22) Filed: May 19, 2017

(65) Prior Publication Data

US 2017/0252496 A1    Sep. 7, 2017

Related U.S. Application Data

(63) Continuation of application No. 15/273,071, filed on Sep. 22, 2016, which is a continuation of application
(Continued)

(30) Foreign Application Priority Data

Oct. 28, 2003    (GB) .................................. 0325129.5

(51) Int. Cl.
*A61M 1/00*    (2006.01)
*A61M 3/02*    (2006.01)
(Continued)

(52) U.S. Cl.
CPC ..... *A61M 1/0088* (2013.01); *A61F 13/00068* (2013.01); *A61F 13/0206* (2013.01);
(Continued)

(58) Field of Classification Search
CPC .............. A61M 1/0088; A61M 1/0068; A61M 1/0072; A61M 1/009; A61M 1/0058; A61F 13/00068; A61F 13/0206
(Continued)

(56) References Cited

U.S. PATENT DOCUMENTS

| | | |
|---|---|---|
| 3,972,328 A | 8/1976 | Chen |
| 4,029,598 A | 6/1977 | Neisius et al. |

(Continued)

FOREIGN PATENT DOCUMENTS

| | | |
|---|---|---|
| DE | 34 43 101 | 5/1986 |
| DE | 198 44 355 | 4/2000 |

(Continued)

OTHER PUBLICATIONS

Kendall ULTEC Hydrocolloid Dressing (4"x4"), product ordering page, web page downloaded Jul. 13, 2014.
(Continued)

*Primary Examiner* — Andrew J Mensh
(74) *Attorney, Agent, or Firm* — Knobbe, Martens, Olson & Bear LLP

(57) ABSTRACT

An apparatus for cleansing wounds, in which wound exudate is removed from a wound bed and selectively cleansed and returned to the wound. The cleansing means removes materials deleterious to wound healing, and the cleansed fluid, still containing materials that are beneficial in promoting wound healing, is returned to the wound bed. The associated wound dressing and cleansing means are conformable to the wound, and may have irrigant fluid circulated from a reservoir by a device for moving fluid through a flow path which passes through the dressing and a means for fluid cleansing and back to the dressing.

24 Claims, 7 Drawing Sheets

Related U.S. Application Data

No. 14/575,968, filed on Dec. 18, 2014, now Pat. No. 9,452,248, which is a continuation of application No. 13/212,039, filed on Aug. 17, 2011, now Pat. No. 9,446,178, which is a continuation of application No. 12/940,788, filed on Nov. 5, 2010, now abandoned, which is a continuation of application No. 10/575,871, filed as application No. PCT/GB2004/004549 on Oct. 28, 2004, now Pat. No. 7,964,766.

(51) Int. Cl.
  *A61M 35/00* (2006.01)
  *A61F 13/00* (2006.01)
  *A61F 13/02* (2006.01)
  *A61M 27/00* (2006.01)

(52) U.S. Cl.
  CPC ...... *A61F 13/0213* (2013.01); *A61F 13/0216* (2013.01); *A61F 13/0259* (2013.01); *A61M 1/009* (2014.02); *A61M 1/0058* (2013.01); *A61M 1/0068* (2014.02); *A61M 1/0072* (2014.02); *A61M 1/0084* (2013.01); *A61M 3/0229* (2013.01); *A61M 35/00* (2013.01); *A61F 2013/00357* (2013.01); *A61M 1/0037* (2013.01); *A61M 1/0062* (2013.01); *A61M 27/00* (2013.01); *A61M 2205/075* (2013.01); *A61M 2205/106* (2013.01); *A61M 2205/7518* (2013.01); *A61M 2205/8206* (2013.01); *Y10T 29/49826* (2015.01)

(58) Field of Classification Search
  USPC .................................................. 604/91, 319
  See application file for complete search history.

(56) References Cited

U.S. PATENT DOCUMENTS

| | | | |
|---|---|---|---|
| 4,813,942 A | 3/1989 | Alvarez | |
| 4,930,997 A * | 6/1990 | Bennett | A61M 1/0019 417/410.1 |
| 5,056,510 A | 10/1991 | Gilman | |
| 5,181,905 A | 1/1993 | Flam | |
| 5,238,732 A | 8/1993 | Krishnan | |
| 5,549,584 A | 8/1996 | Gross | |
| 5,662,924 A * | 9/1997 | Rhodes | 424/445 |
| 5,707,499 A | 1/1998 | Joshi et al. | |
| 5,759,570 A | 6/1998 | Arnold | |
| 6,071,267 A | 6/2000 | Zamierowski | |
| 6,626,891 B2 | 9/2003 | Ohmstede | |
| 6,685,681 B2 | 2/2004 | Lockwood et al. | |
| 6,752,794 B2 | 6/2004 | Lockwood et al. | |
| 6,936,037 B2 | 8/2005 | Bubb et al. | |
| 6,951,553 B2 | 10/2005 | Bubb et al. | |
| 6,979,324 B2 | 12/2005 | Bybordi et al. | |
| 7,004,915 B2 | 2/2006 | Boynton et al. | |
| 7,108,683 B2 | 9/2006 | Zamierowski | |
| 7,216,651 B2 | 5/2007 | Argenta et al. | |
| 7,361,184 B2 | 4/2008 | Joshi | |
| 7,381,859 B2 | 6/2008 | Hunt et al. | |
| 7,569,742 B2 | 8/2009 | Haggstrom et al. | |
| 7,605,298 B2 | 10/2009 | Bechert et al. | |
| 7,615,036 B2 | 11/2009 | Joshi et al. | |
| 7,622,629 B2 | 11/2009 | Aail | |
| 7,625,362 B2 | 12/2009 | Boehringer et al. | |
| 7,699,823 B2 | 4/2010 | Haggstrom et al. | |
| 7,700,819 B2 | 4/2010 | Ambrosio et al. | |
| 7,708,724 B2 | 5/2010 | Weston | |
| 7,718,249 B2 | 5/2010 | Russell et al. | |
| 7,722,582 B2 | 5/2010 | Lina et al. | |
| 7,749,531 B2 | 7/2010 | Booher | |
| 7,759,537 B2 | 7/2010 | Bishop et al. | |
| 7,759,539 B2 | 7/2010 | Shaw et al. | |
| 7,775,998 B2 | 8/2010 | Riesinger | |
| 7,779,625 B2 | 8/2010 | Joshi et al. | |
| 7,811,269 B2 | 10/2010 | Boynton et al. | |
| 7,838,717 B2 | 11/2010 | Haggstrom et al. | |
| 7,846,141 B2 | 12/2010 | Weston | |
| 7,910,791 B2 | 3/2011 | Coffey | |
| 7,922,703 B2 | 4/2011 | Riesinger | |
| 7,959,624 B2 | 6/2011 | Riesinger | |
| 7,964,766 B2 | 6/2011 | Blott et al. | |
| 7,976,519 B2 | 7/2011 | Bubb et al. | |
| 8,034,037 B2 | 10/2011 | Adams et al. | |
| 8,062,272 B2 | 11/2011 | Weston | |
| 8,062,331 B2 | 11/2011 | Zamierowski | |
| 8,080,702 B2 | 12/2011 | Blott et al. | |
| 8,118,794 B2 | 2/2012 | Weston et al. | |
| 8,152,785 B2 | 4/2012 | Vitaris | |
| 8,282,611 B2 | 10/2012 | Weston | |
| 8,303,552 B2 | 11/2012 | Weston | |
| 8,323,265 B2 | 12/2012 | Heaton | |
| 8,460,255 B2 | 6/2013 | Joshi et al. | |
| 8,628,505 B2 | 1/2014 | Weston | |
| 8,715,256 B2 | 5/2014 | Greener | |
| 8,764,732 B2 | 7/2014 | Hartwell | |
| 8,795,243 B2 | 8/2014 | Weston | |
| 8,808,274 B2 | 8/2014 | Hartwell | |
| 8,829,263 B2 | 9/2014 | Haggstrom et al. | |
| 8,834,451 B2 | 9/2014 | Blott et al. | |
| 8,834,452 B2 | 9/2014 | Hudspeth et al. | |
| 8,956,336 B2 | 2/2015 | Haggstrom et al. | |
| 9,012,714 B2 | 4/2015 | Fleischmann | |
| 9,061,095 B2 | 6/2015 | Adie et al. | |
| 9,168,330 B2 | 10/2015 | Joshi et al. | |
| 9,199,012 B2 | 12/2015 | Vitaris et al. | |
| 9,220,822 B2 | 12/2015 | Hartwell et al. | |
| 9,375,353 B2 | 6/2016 | Vitaris et al. | |
| 9,375,521 B2 | 6/2016 | Hudspeth et al. | |
| 9,446,178 B2 | 9/2016 | Blott et al. | |
| 9,452,248 B2 | 9/2016 | Blott et al. | |
| 2002/0115952 A1 | 8/2002 | Johnson et al. | |
| 2003/0125646 A1 | 7/2003 | Whitlock | |
| 2004/0030304 A1 * | 2/2004 | Hunt | A61M 1/0088 604/317 |
| 2004/0057855 A1 | 3/2004 | Gerlach et al. | |
| 2004/0127836 A1 | 7/2004 | Sigurjonsson et al. | |
| 2005/0010153 A1 | 1/2005 | Lockwood et al. | |
| 2006/0009744 A1 | 1/2006 | Edrman et al. | |
| 2007/0225663 A1 | 9/2007 | Watt et al. | |
| 2008/0132821 A1 | 6/2008 | Propp et al. | |
| 2008/0306456 A1 | 12/2008 | Riesinger | |
| 2009/0234306 A1 | 9/2009 | Vitaris | |
| 2009/0299251 A1 | 12/2009 | Buan | |
| 2011/0118683 A1 | 5/2011 | Weston | |
| 2012/0209224 A1 | 8/2012 | Weston | |
| 2013/0138054 A1 | 5/2013 | Fleischmann | |
| 2013/0150814 A1 | 6/2013 | Buan | |
| 2013/0274688 A1 | 10/2013 | Weston | |
| 2014/0228791 A1 | 8/2014 | Hartwell | |
| 2014/0236109 A1 | 8/2014 | Greener | |
| 2015/0065965 A1 | 3/2015 | Haggstrom et al. | |
| 2015/0209492 A1 | 7/2015 | Blott et al. | |
| 2015/0320604 A1 | 11/2015 | Adie et al. | |
| 2016/0051737 A1 | 2/2016 | Joshi et al. | |
| 2016/0081859 A1 | 3/2016 | Hartwell | |
| 2016/0298620 A1 | 10/2016 | Cordoba et al. | |
| 2016/0317357 A1 | 11/2016 | Vitaris et al. | |
| 2017/0007753 A1 | 1/2017 | Blott et al. | |
| 2017/0095598 A1 | 4/2017 | Joshi et al. | |
| 2017/0128642 A1 | 5/2017 | Buan | |
| 2019/0091383 A1 | 3/2019 | Weston | |

FOREIGN PATENT DOCUMENTS

| | | |
|---|---|---|
| DE | 20 2004 017 052 | 7/2005 |
| EP | 0 257 916 | 3/1988 |
| EP | 0 340 018 | 11/1989 |
| EP | 1 476 217 | 3/2008 |
| EP | 1 955 887 | 8/2008 |
| FR | 1 163 907 | 10/1958 |
| GB | 1255395 | 12/1971 |

(56) References Cited

FOREIGN PATENT DOCUMENTS

| WO | WO 1983/00742 | 3/1983 |
|----|---------------|--------|
| WO | WO 1995/29959 | 11/1995 |
| WO | WO 1996/05873 | 2/1996 |
| WO | WO 2004/077387 | 9/2004 |
| WO | WO 2005/025447 | 3/2005 |
| WO | WO 2005/123170 | 12/2005 |

OTHER PUBLICATIONS

Membrane Filters, in 16 pages, from website: http://www.advantecmfs.com/catalog/filt/membrane.pdf#page=11 (date unknown, but believed to be copyright 2001-2011).

Protz, Kerstin: "Modern Wundauflagen unterstutzen Heilungsprozess", Wundversorgung: Indikation and Anwendung, Geriatrie Journal, Apr. 2005, pp. 3333-3339, with translation.

"Technology Watch", May 1989, in 1 page.

Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.

U.S. Appl. No. 16/201,508, filed Nov. 27, 2018, Walton et al.

* cited by examiner

WOUND CLEANSING APPARATUS IN-SITU

CROSS-REFERENCE TO RELATED APPLICATIONS

This application is a continuation of U.S. patent application Ser. No. 15/273,071, published as U.S. 2017/0007753 A1 and filed on Sep. 22, 2016, which is a continuation of U.S. patent application No. 14/575,968, filed on Dec. 18, 2014, now U.S. Pat. No. 9,452,248, which is a continuation of U.S. patent application Ser. No. 13/212,039, filed on Aug. 17, 2011, now U.S. Pat. No. 9,446,178, which is a continuation of U.S. patent application Ser. No. 12/940,788, published as US 2011/0054423 A1 and filed on Nov. 5, 2010, now abandoned, which is a continuation of U.S. patent application Ser. No. 10/575,871, filed on Jan. 29, 2007, now U.S. Pat. No. 7,964,766, which is a U.S. National Phase of the PCT International Application No. PCT/GB2004/004549, filed on Oct. 28, 2004, and which claims priority to application GB 0325129.5, filed on Oct. 28, 2003. The entirety of these preceding disclosures are hereby incorporated by reference.

FIELD OF THE INVENTION

The present invention relates to apparatus and a medical wound dressing for cleansing wounds, and a method of treating wounds using such apparatus.

It relates in particular to such an apparatus, wound dressing and method that can be easily applied to a wide variety of, but in particular chronic, wounds, to cleanse them of materials that are deleterious to wound healing, whilst retaining materials that are beneficial in particular to wound healing.

BACKGROUND OF THE INVENTION

Before the present invention, aspirating and/or irrigating apparatus were known, and tended to be used to remove wound exudate during wound therapy. In known forms of such wound therapy, the offtake from the wound, especially when in a highly exuding state, is voided to waste, e.g. to a collection bag.

Materials deleterious to wound healing are removed in this way. However, materials that are beneficial in promoting wound healing, such as growth factors, cell matrix components, and other physiologically active components of the exudate from a wound are lost to the site where they can be potentially of most benefit, i.e. the wound bed, when such therapy is applied.

Such known forms of wound dressing and aspiration and/or irrigation therapy systems thus often create a wound environment under the dressing that may result in the loss of optimum performance of the body's own tissue healing processes and in slow healing, and/or in weak new tissue growth that does not have a strong three-dimensional structure adhering well to and growing from the wound bed. This is a significant disadvantage, in particular in chronic wounds.

It thus would be desirable to provide a system of therapy which a) can remove materials deleterious to wound healing from wound exudate, whilst retaining materials that are beneficial in promoting wound healing in contact with the wound bed.

Dialysis is a known method of treating bodily fluids such as blood ex vivo, to cleanse them of materials that are deleterious to the body systemically. Removal of such materials by contact with the dialysate is the prime purpose of dialysis, whilst also retaining materials such as blood, cells and proteins. Other materials that may have an additional positive therapeutic action are potentially lost to the system through the dialysis membrane, which is also permeable to them. The balance of such materials in the bodily fluid in recirculation may thus be further depleted.

SUMMARY OF THE INVENTION

It would be desirable to provide a system of therapy that can remove materials deleterious to wound healing from wound exudate, without substantially diluting materials that are beneficial in promoting wound healing in contact with the wound bed, and which can continuously supply and recirculate such materials to the wound simultaneously.

Dialysis for treating bodily fluids is also a systemic therapy, since the treated fluid is returned to within the body. This is in contrast to a topical therapy in which the treated fluid is recycled outside the body, e.g. to a wound.

Dialysis also requires large amounts either of bodily fluids, such as blood, or dialysate, and consequently the relevant devices tend not to be portable. Even when in a highly exuding state, chronic wounds produce relatively little fluid to be treated compared with internal bodily systems and relatively little materials that are beneficial in some therapeutic aspect to be retained in the wound and/or its environment.

It is an object of the present invention to obviate at least some of the abovementioned disadvantages of known aspiration and/or irrigation therapy systems, and to provide a system of therapy which can i) remove materials deleterious to wound healing from wound exudate, whilst ii) retaining materials that are beneficial in promoting wound healing in contact with the wound bed.

It is a further object of the present invention to obviate at least some of the abovementioned disadvantages of known dialysis systems, and to provide a system of therapy which can remove materials deleterious to wound healing from wound exudate, whilst retaining materials that are beneficial in promoting wound healing in contact with the wound bed, without affecting the body systemically.

It is a yet further object of the present invention to obviate at least some of the abovementioned disadvantages of known dialysis systems, and to provide a system of therapy which can remove materials deleterious to wound healing from wound exudate, whilst retaining materials that are beneficial in promoting wound healing in contact with the wound bed, and is portable.

Vascular supply to, and circulation in, tissue underlying and surrounding the wound is often compromised. It is a further object of the present invention to provide a system of therapy that retains and supplies therapeutically active amounts of materials that are beneficial in reversing this effect whilst removing deleterious materials, thereby promoting wound healing.

Thus, according to a first aspect of the present invention there is provided an apparatus for cleansing wounds, comprising a conformable wound dressing, having a backing layer which is capable of forming a relatively fluid-tight seal or closure over a wound and characterised in that it also comprises a cleansing means for selectively removing materials that are deleterious to wound healing from wound exudate, which means is under the backing layer and sits in the underlying wound in use and a moving device for moving fluid through the cleansing means, and optionally bleed means for bleeding the cleansing means.

The term 'bleed means for bleeding the cleansing means' includes any bleed means that is in fluidic communication with the cleansing means.

Materials deleterious to wound healing are removed by the cleansing means, and the cleansed fluid remains in and/or is returned to the wound.

The fluid thus retains naturally occurring materials in the wound exudate that are potentially beneficial to wound healing in therapeutically active amounts The apparatus for cleansing wounds of this first aspect of the present invention is based on this principle: by moving fluid through the cleansing means, the moving device continually brings materials that are deleterious to wound healing and the cleansing means into mutual dynamic contact, rather than relying on the passive movement of such materials, e.g. by diffusion under a chemical potential gradient in a fluid. Their removal from the wound exudate occurs more rapidly with such fluid movement.

There are various embodiments of the apparatus of the first aspect of the present invention for different types of application, including in particular those that are described in detail hereinafter. No matter how different they may be, it is believed that they may be classified into the following functional types, typified by which fluid passes through the cleansing means:

1. A 'Single-Phase System'

In this, the fluid that is moved through the means for fluid cleansing is wound exudate optionally mixed with an irrigant. This passes into, through and out of the cleansing means, e.g. a chamber under the backing layer, and back to the wound bed. Materials deleterious to wound healing pass into and are removed by the means for fluid cleansing before return of the cleansed fluid to the wound bed.

2. A 'Multiple-Phase System'

In this, the wound exudate remains in the wound, and does not pass into the cleansing means on a macro-scale. The means for fluid cleansing often comprises a chamber containing a second, cleansing fluid, most usually a fluid (dialysate) phase. The latter is separated from the wound exudate by means of a permeable integer, for example often a polymer film, sheet or membrane. The fluid that is moved through the means for fluid cleansing by the device for moving fluid is the cleansing fluid and/or the wound exudate optionally mixed with irrigant.

In both single- and multiple-phase systems, it may be appropriate to design and run the device to move fluid through the wound or the cleansing means to operate the system as a 'circulating system'.

In this, the relevant fluid passes through the cleansing means one or more times in only one direction.

Alternatively, where appropriate it may be provided in the form of a 'reversing system'. That is, the relevant fluid passes through the cleansing means at least once in opposing directions.

The apparatus of the first aspect of the present invention may however in different types of application be operated both as a circulating system and as a reversing system, in which the relevant fluid passes through the cleansing means at least once in the same and in opposing directions. (See FIG. 2 hereinafter).

The type of cleansing means may determine the appropriate design and mode of running the present apparatus.

The cleansing means may as desired be operated as a 'single-pass system', i.e. the relevant fluid passes through the cleansing means only once.

Alternatively, where appropriate it may be provided in the form of a 'multiple-pass system', in which the relevant fluid passes through the cleansing means and/or over the wound bed several times.

It will be seen that the combination of these parameters create a number of main embodiments of the present invention. In summary, these are:

1. A 'Single-Phase System' a) as a 'circulating system', in which the wound exudate and optionally irrigant passes through the cleansing means one or more times in only one direction (Examples of such a system are shown in FIGS. 2, 4, 8, 9, 11 and 15 hereinafter.), or b) as a 'reversing system', i.e. the wound exudate and optionally irrigant passes through the cleansing means at least once in opposing directions. (Examples of such a system are shown in FIGS. 1, 2, 3, 6, 7, 10 and 14 hereinafter.)

This type of cleansing may be operated as a i) 'single-pass system', i.e. the relevant fluid passes through the cleansing means only once, or ii) as 'multiple-pass system', in which the relevant fluid passes through the cleansing means and/or over the wound bed several times.

2. A 'Multiple-Phase System' as a 'circulating system', in which (i) the wound exudate and optionally irrigant and/or (ii) a cleansing fluid each passes through the cleansing means one or more times in only one direction (Examples of such a system are shown in FIGS. 12 and 13 hereinafter.), or as a 'reversing system', i.e.

(i) the wound exudate and optionally irrigant and/or (ii) a cleansing fluid each passes through the cleansing means at least once in opposing directions.

This type of cleansing may be operated as a i) 'single-pass system', i.e. the relevant fluid passes through the cleansing means only once, or ii) as 'multiple-pass system', in which the relevant fluid passes through the cleansing means and/or over the wound bed several times.

In such a 'multiple-phase system', where both the cleansing fluid and/or the wound exudate optionally mixed with irrigant are moving, the flows may be cocurrent or countercurrent, preferably countercurrent.

Examples of such circulating systems are shown in:

FIGS. 12a and 13 in which the exudate is static and a cleansing fluid passes through the cleansing means one or more times in only one direction, and FIG. 12b, in which the exudate and optionally irrigant and a cleansing fluid each pass through the cleansing means one or more times in only one direction, here countercurrent to each other.

The general features of the dressing of the present invention will now be described, followed by specific features related to specific cleansing means within the dressing.

In all embodiments of the apparatus of this first aspect of the present invention for cleansing wounds, a particular advantage is the tendency of the wound dressing to conform to the shape of the bodily part to which it is applied.

The wound dressing comprises a backing layer with a wound-facing face which is capable of forming a relatively fluid-tight seal or closure over a wound.

The term 'relatively fluid-tight seal or closure' is used herein to indicate one which is fluid- and microbe-impermeable and permits a positive or negative pressure of up to 50% atm., more usually up to 15% atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to aspirating, irrigating and/or cleansing the wound across the area of the wound.

Examples of such include a substantially flat film, sheet or membrane, or a bag, chamber, pouch or other structure of the backing layer, e.g. of polymer film, which can contain the necessary fluids.

The backing layer may be a film, sheet or membrane, often with a (generally uniform) thickness of up to 100 micron, preferably up to 50 micron, more preferably up to 25 micron, and of 10 micron minimum thickness.

Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound.

Suitable materials for it include synthetic polymeric materials that do not absorb aqueous fluids, such as polyolefins, such as polyethylene e.g. high-density polyethylene, polypropylene, copolymers thereof, for example with vinyl acetate and polyvinyl alcohol, and mixtures thereof;

polysiloxanes;

polyesters, such as polycarbonates;

polyamides, e.g. 6-6 and 6-10, and hydrophobic polyurethanes.

They may be hydrophilic, and thus also include hydrophilic polyurethanes.

They also include thermoplastic elastomers and elastomer blends, for example copolymers, such as ethyl vinyl acetate, optionally or as necessary blended with high-impact polystyrene.

They further include elastomeric polyurethane, particularly polyurethane formed by solution casting.

Preferred materials for the present wound dressing include thermoplastic elastomers and curable systems.

The backing layer is capable of forming a relatively fluid-tight seal or closure over the wound and/or around the inlet and outlet pipe(s).

However, in particular around the periphery of the wound dressing, outside the relatively fluid-tight seal, it is preferably of a material that has a high moisture vapour permeability, to prevent maceration of the skin around the wound. It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound.

This may, e.g. be a pressure-sensitive adhesive, if that is sufficient to hold the wound dressing in place in a fluid-tight seal around the periphery of the wound-facing face of the wound dressing.

Alternatively or additionally, where appropriate a light switchable adhesive could be used to secure the dressing in place to prevent leakage. (A light switchable adhesive is one the adhesion of which is reduced by photocuring. Its use can be beneficial in reducing the trauma of removal of the dressing.)

Thus, the backing layer may have a flange or lip extending around the proximal face of the backing layer, of a transparent or translucent material (for which it will be understood that materials that are listed above are amongst those that are suitable).

This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the wound is removed prior to application of radiation of an appropriate wavelength to the flange or lip.

If the periphery of the wound dressing, outside the relatively fluid-tight seal, that bears an adhesive film to attach it to the skin around the wound, is of a material that has a high moisture vapour permeability or is a switchable material, then the adhesive film, if continuous, should also have a high or switchable moisture vapour permeability, e.g. be an adhesive such as used in Smith & Nephew's Allevyn™ IV3000™ and OpSite™ dressings.

In a number of main embodiments of the present invention (summarised above), irrigant and/or wound exudate is moved in and out of the dressing.

This may be done under negative pressure on the dressing. Such a vacuum may be used to hold the wound dressing in place in a fluid-tight seal around the periphery of the wound-facing face of the wound dressing.

This removes the need for adhesives and associated trauma to the patient's skin, and the wound dressing may be merely provided with a silicone flange or lip to seal the dressing around the wound.

Alternatively, the flow of irrigant and/or wound exudate in and out of the dressing may be under positive pressure, which will tend to act at peripheral points to lift and remove the dressing off the skin around the wound.

In such use of the apparatus, it may thus be necessary to provide means for forming and maintaining such a seal or closure over the wound against such positive pressure on the wound, to act at peripheral points for this purpose.

Examples of such means include light switchable adhesives, as above, to secure the dressing in place to prevent leakage.

Since the adhesion of a light switchable adhesive is reduced by photocuring, thereby reducing the trauma of removal of the dressing, a film of a more aggressive adhesive may be used, e.g. on a flange, as above.

Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip.

Further suitable examples of such means include adhesive (e.g. with pressure-sensitive adhesive) and non-adhesive, and elastic and non-elastic straps, bands, loops, strips, ties, bandages, e.g. compression bandages, sheets, covers, sleeves, jackets, sheaths, wraps, stockings and hose.

The latter include, e.g. elastic tubular hose or elastic tubular stockings that are a compressive fit over a limb wound to apply suitable pressure to it when the therapy is applied in this way.

Suitable examples also include inflatable cuffs, sleeves, jackets, trousers, sheaths, wraps, stockings and hose that are a compressive fit over a limb wound to apply suitable pressure to it when the therapy is applied in this way.

Such means may each be laid out over the wound dressing to extend beyond the periphery of the backing layer of the wound dressing.

As appropriate they may be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound, Such means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The means and the dressing may be separate structures, permanently unattached to each other.

In a more suitable layout for higher positive pressures on the wound, a stiff flange or lip extends around the periphery of the proximal face of the backing layer of the wound dressing as hereinbefore defined.

The flange or lip is concave on its proximal face to define a peripheral channel or conduit.

It has a suction outlet that passes through the flange or lip to communicate with the channel or conduit and may be connected to a device for applying a vacuum, such as a pump or a piped supply of vacuum.

The backing layer may be integral with or attached, for example by heat-sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound.

The device then applies a vacuum to the interior of the flange or lip, thus forming and maintaining a seal or closure acting at peripheral points around the wound against the positive pressure on the wound.

With all the foregoing means of attachment, and means for forming and maintaining a seal or closure over the wound, against positive or negative pressure on the wound at peripheral points around the wound, the wound dressing sealing periphery is preferably of a generally round shape, such as an ellipse, and in particular circular.

As noted above, the cleansing means for selectively removing materials that are deleterious to wound healing from wound exudate, which means is under the backing layer and sits in the underlying wound in use, often comprises a chamber. A permeable integer, e.g. a sheet, film or membrane, forms part of the chamber wall.

In single-phase systems, the device to move fluid moves wound exudate in and out of the cleansing means through the permeable integer, either as a 'circulating system' or a reversing system.

In two-phase systems, the chamber contains a cleansing fluid, most usually a fluid (dialysate) phase. The latter is separated from the wound exudate by means of the permeable integer. The fluid that is moved within the means for fluid cleansing by at least one device for moving fluid is the cleansing fluid. and/or the wound exudate optionally mixed with irrigant.

The general features of the cleansing means of the present invention will now be described, followed by specific features related to specific cleansing means within the dressing.

The cleansing chamber is a resiliently flexible, e.g. elastomeric, and preferably soft, structure with good conformability to wound shape.

It is favourably urged by its own resilience against the backing layer to apply gentle pressure on the wound bed.

The cleansing chamber may be integral with the other components of the dressing, in particular the backing layer.

Alternatively, it may be permanently attached to them/it, with an adhesive film, for example, or by heat-sealing, e.g. to a flange or lip extending from the proximal face, so as not to disrupt the relatively fluid-tight seal or closure over the wound that is needed.

Less usually, the cleansing chamber is releasably attached to the backing layer, with an adhesive film, for example, or these components may be a push, snap or twist-lock fit with each other.

The cleansing chamber and the backing layer may be separate structures, permanently unattached to each other.

It may be in the form of, or comprise one or more conformable hollow bodies defined by a film, sheet or membrane, such as a bag, cartridge, pouch or other like structure.

The film, sheet or membrane, often has a (generally uniform) thickness of up to 1 mm, preferably up to 500 micron, more preferably from 20 micron to 500 micron minimum thickness, and is often resiliently flexible, e.g. elastomeric, and preferably soft.

Such a film, sheet or membrane is often integral with the other components of the dressing, in particular the backing layer, or permanently attached to them/it, with an adhesive film, for example, or by heat-sealing, e.g. to a flange.

However, when used herein the term 'chamber' includes any hollow body or bodies defined by a film, sheet or membrane, and is not limited to a bag, pouch or other like structure.

It may be formed of a film, sheet or membrane of a polymeric material is in a more convoluted form.

This may be in the form of elongate structures, such as pipes, tubes hollow fibres or filaments or tubules, e.g. in an array with spaces therebetween, running between an inlet and an outlet manifold.

The chamber, especially when it is a bag, cartridge, pouch or other like structure in which the cleansing fluid is contained, may suitably fill much or all of the wound space when in use during wound therapy. It may be desired to limit the remaining wound space volume under the backing layer with a filler where this is not the case, or to adjust the volume of the chamber to do so.

Where the chamber and the backing layer are separate structures, not directly attached to each other, such a filler may conveniently lie between the chamber and the backing layer to separate the structures, or within the chamber, so that the chamber may lie directly in contact with the wound bed.

The filler is favourably a resiliently flexible, e.g. elastomeric, and preferably soft, structure with good conformability to wound shape. The chamber may be urged by its own resilience and that of the filler to apply gentle pressure on the wound bed.

Examples of suitable forms of such wound fillers include foams formed of a suitable material, e.g. a resilient thermoplastic. Preferred materials for the present wound dressing include reticulated filtration polyurethane foams with small apertures or pores. (Examples of such a filler are shown in FIGS. 7, 10, 11 and 13 hereinafter.)

Alternatively or additionally, it may be in the form of, or comprise one or more conformable hollow bodies defined by a film, sheet or membrane, such as a bag, pouch or other structure, filled with a fluid or solid that urges it to the wound shape.

Examples of suitable fluids contained in the hollow body or bodies defined by a film, sheet or membrane include gases, such as air, nitrogen and argon, more usually air, at a small positive pressure above atmospheric; and liquids, such as water, saline.

Examples also include gels, such as silicone gels, e.g. CaviCare™ gel, or preferably cellulosic gels, for example hydrophilic cross-linked cellulosic gels, such as Intrasite™ cross-linked materials. Examples also include aerosol foams, where the gaseous phase of the aerosol system is air or an inert gas, such as nitrogen or argon, more usually air, at a small positive pressure above atmospheric; and solid particulates, such as plastics crumbs.

Such a filler may be inflatable and deflatable with the fluid, such as a gas, e.g. air or nitrogen, or a liquid, such as water or saline, to apply varying pressure to the chamber and wound space if provided with one or more inlet and/or outlet pipes.

Of course, if the backing layer is a sufficiently conformable and/or e.g. a downwardly dished sheet, the backing layer may lie under the wound filler, rather than vice versa. FIG. 6 shows such a resiliently flexible, balloon filler, which is inflatable and deflatable with a fluid, defined by the backing layer and a rigid polymer dome that is impermeable and permanently attached to the distal face of the backing layer In this type of layout, in order for the wound filler to urge the wound dressing towards the wound bed, it will usually have to be firmly adhered or otherwise releasably attached to the skin around the wound. This is especially the case in those embodiments where the wound filler and the backing layer are separate structures, permanently unattached to each other. FIG. 7 shows a variant of the apparatus with such a resiliently flexible balloon filler above the backing layer.

The specific nature of the chamber will depend largely on the type of cleansing means that is employed.

The apparatus of the invention for aspirating, irrigating and/or cleansing wounds is provided with means for fluid cleansing, which may be a) a single-phase system, such as an ultrafiltration unit, or a chemical adsorption unit; or b) a two-phase system, such as a dialysis unit.

In the former, fluid from the wound passes through a single flow path in which materials deleterious to wound healing are removed and the cleansed fluid, still containing materials that are beneficial in promoting wound healing is returned to the wound.

Examples of such systems are shown in FIGS. 1 and 2 hereinafter.

The means for fluid cleansing in such a system may include a macro- or microfiltration unit, which appropriately comprises one or more macroscopic and/or microscopic filters. These are to retain particulates, e.g. cell debris and micro-organisms, allowing proteins and nutrients to pass through.

The membrane may preferably be of a hydrophilic polymeric material, such as a cellulose acetate—nitrate mixture, polyvinylidene chloride, and, for example hydrophilic polyurethane.

Examples of less preferred materials include hydrophobic materials also including polyesters, such as polycarbonates, PTFE, and polyamides, e.g. 6-6 and 6-10, and hydrophobic polyurethanes, and quartz and glass fibre.

It has microapertures or micropores, the maximum cross-dimension of which will largely depend on the species that are to be selectively removed in this way and those to which it is to be permeable.

The former may be removed with microapertures or micropores, e.g. typically with a maximum cross-dimension in the range of 20 to 700 micron, e.g. 20 to 50 nm (for example for undesired proteins), 50 to 100 nm, 100 to 250 nm, 250 to 500 nm and 500 to 700 nm.

Alternatively, this part of a means for wound exudate cleansing may be essentially a stack of such filters connected in series with decreasing cross-dimension of the apertures or pores in the direction of the fluid flow.

It may include an ultrafiltration unit, which appropriately comprises one or more ultrafiltration filters, such as one in which the cleansing integer is a filter for materials deleterious to wound healing, for example a high throughput, low protein-binding polymer film, sheet or membrane which is selectively impermeable to materials deleterious to wound healing, which are removed and the cleansed fluid, still containing materials that are beneficial in promoting wound healing is passed by it.

The permeable integer in such a system may be a selective 'low pass' system film, sheet or membrane with relatively small apertures or pores.

Suitable materials for the filter include those organic polymers listed above for macro- and micro-filters.

It will be appropriate to design and run the apparatus with this type of cleansing means as a 'circulating system', in which the relevant fluid passes through the cleansing means one or more times in only one direction, since this is necessary for retaining the filter residue out of the wound exudate.

(It would be inappropriate to run the system in the form of a 'reversing system', since the fluid passing through the cleansing means at least once in the reverse direction would return these materials into the wound.)

The filter integer may be a flat sheet or membrane of a polymeric material, or (less usually) in a more convoluted form, e.g. in the form of elongate structure, such as pipes, tubules, etc.

It may be intended that respectively the chamber or the dressing is disposable. In such case, the device for moving fluid through the means for wound exudate cleansing is then started and run until no significant amounts of materials deleterious to wound healing remain in the wound.

The dressing and/or the cleansing chamber under the backing layer is then removed and discarded, to remove the materials deleterious to wound healing from wound exudate.

A single-phase system cleansing means may comprise a chemical adsorption unit, for example one in which a particulate, such as a zeolite, or a layer, e.g. of a functionalised polymer has sites on its surface that are capable of removing materials deleterious to wound healing on passing the fluid from the wound over them.

The materials may be removed, e.g. by destroying or binding the materials that are deleterious to wound healing, by, for example chelators and/or ion exchangers, and degraders, which may be enzymes.

In this type, the chamber wall film, sheet or membrane is not an integer selectively permeable to materials deleterious to wound healing. The chamber, however, contains one or more materials that can remove materials deleterious to wound healing from wound exudate, by being antagonists to such species.

For example, where the wound exudate contains proteases, such as serine proteases, e.g. elastase, and thrombin; cysteine proteases, matrix metalloproteases, e.g. collagenase; and carboxyl (acid) proteases;

endotoxins, such as lipopolysaccharides;

inhibitors of angiogenesis such as thrombospondin-1 (TSP-1), plasminogen activator inhibitor, or angiostatin (plasminogen fragment);

pro-inflammatory cytokines such as tumour necrosis factor alpha (TNFα) and interleukin 1 beta (IL-1β), oxidants, such as free radicals, e.g., e.g. peroxide and superoxide; and metal ions, e.g. iron II and iron III; all involved in oxidative stress on the wound bed, or basic or acidic species which adversely affect the pH in the wound exudate, such as protons, the cleansing chamber may contain, behind the permeable integer at least one of the following antagonists as appropriate that is captive in a part of the chamber where it can be in contact with the irrigant and/or wound exudate:

protease inhibitors, such as serine protease inhibitors, such as 4-(2-aminoethyl)-benzene sulphonyl fluoride (AEBSF, PefaBloc) and Nα-p-tosyl-L-lysine chloromethyl ketone (TLCK) and ε-aminocaproyl-p-chlorobenzylamide; cysteine protease inhibitors; matrix metalloprotease inhibitors; and carboxyl (acid) protease inhibitors;

binders and/or degraders, such as anti-inflammatory materials to bind or destroy lipopolysaccharides, e.g. peptidomimetics;

anti-oxidants, such as 3-hydroxytyramine (dopamine), ascorbic acid (vitamin C), vitamin E and glutathione, and stable derivatives thereof, and mixtures thereof; to relieve oxidative stress on the wound bed:

metal ion chelators and/or ion exchangers, such as transition metal ion chelators, such as iron III chelators (Fe III is involved in oxidative stress on the wound bed.), such as desferrioxamine (DFO), 3-hydroxytyramine (dopamine);

iron III reductants; or agents for the adjustment of pH in the wound exudate, such as base or acid scavengers and/or ion exchangers, or other species, which may be non-labile, insoluble and/or immobilised) species, such as ScavengePore® phenethyl morpholine (Aldrich).

It will be appropriate to design and run the apparatus with this type of cleansing means either as a 'circulating system', or in the form of a 'reversing system', since the fluid passing through the cleansing means at least once in the reverse direction would not return these materials into the wound.)

An example of such systems is shown inter alia in FIGS. 1, 6 and 7 (reversing system) and 2, 8 and 9 (circulating system) hereinafter.

A second, selectively permeable integer, again suitably a flat sheet or membrane of a polymeric material may be required to form part of a distal chamber wall in the flowpath in any appropriate part of the apparatus to retain materials that are deleterious to wound healing and antagonists or other active materials in the chamber.

A particular advantage of this form of the system, is that where a material that can remove materials deleterious to wound healing from wound exudate is (cyto)toxic or bioincompatible, or not inert to any components that are beneficial in promoting wound healing, the system does not allow any significant amounts of it to pass into the wound.

In two-phase systems, the chamber contains a cleansing fluid, most usually a fluid (dialysate) phase. The latter is separated from the wound exudate by means of a permeable integer.

At least one fluid is moved through the means for fluid cleansing by at least one device, in particular across the permeable integer, for example the polymer film, sheet or membrane.

This promotes the passage of relatively high concentrations of solutes or disperse phase species, including deleterious materials, from the wound exudate into the cleansing fluid and the chamber and optionally the system in which the cleansing fluid recirculates. Such systems are described further below.

The fluid that is moved through the means for fluid cleansing by the device for moving fluid is a) the cleansing fluid or b) the wound exudate optionally mixed with irrigant, or c) both.

Examples of such systems are shown in FIGS. 12 and 13 hereinafter, in which

FIGS. 12a and 13 show such a system, a dialysis unit, in which only the cleansing fluid separated from the wound exudate is the moving fluid.

FIG. 12b shows such a system, a dialysis unit, in which the cleansing fluid and the wound exudate optionally with irrigant are the moving fluids.

The cleansing fluid is less usually static as in FIG. 4, as this may not be a system with sufficient (dynamic) surface area to remove materials deleterious to wound healing from wound exudate at a practical rate.

Typical dialysate flow rates in a dialytic means for fluid cleansing in the present apparatus for aspirating, irrigating and/or cleansing wounds are those used in the conventional type of two-phase system, such as a dialysis unit for systemic therapy.

The integer may be a film, sheet or membrane, often of the same type, and of the same (generally uniform) thickness, as those used in conventional two-phase system, such as a dialysis unit for systemic therapy.

As noted above, the film, sheet or membrane may be substantially flat, but, especially where the cleansing fluid circulates, it may more suitably be in the form of pipes, tubes or tubules in an array.

The surface area of any such film, sheet or membrane may be suitably be no less than 50 mm2, such 100 to 1000000 mm2, e.g. 500 to 25000 mm2.

If both fluids move it may be in co- or preferably counter-current direction.

Again, materials deleterious to wound healing are removed into the dialysate, and the cleansed fluid, still containing materials that are beneficial in promoting wound healing, remains or is returned by recirculation to the wound.

Examples of these deleterious materials as above include oxidants, such as free radicals, e.g. peroxide and superoxide;

iron II and iron III; all involved in oxidative stress on the wound bed;

proteases, such as serine proteases, e.g. elastase and thrombin; cysteine proteases, matrix metalloproteases, e.g. collagenase; and carboxyl (acid) proteases;

endotoxins, such as lipopolysaccharides;

autoinducer signalling molecules, such as homoserine lactone derivatives, e.g. oxo-alkyl derivatives;

inhibitors of angiogenesis such as thrombospondin-1 (TSP-1), plasminogen activator inhibitor, or angiostatin (plasminogen fragment)

pro-inflammatory cytokines such as tumour necrosis factor alpha (TNFα) and interleukin 1 beta (IL-1β); and inflammatories, such as lipopolysaccharides, and e.g. histamine; and basic or acidic species which adversely affect the pH in the wound exudate, such as protons.

Examples of suitable materials for the film, sheet or membrane (typically in the form of conformable hollow bodies defined by the film, sheet or membrane, such as the structures described hereinbefore) include natural and synthetic polymeric materials.

The membrane may be of one or more hydrophilic polymeric materials, such as a cellulose derivative, e.g. regenerated cellulose, a cellulose mono-, di- or tri- esters, such as cellulose mono-, di- or tri-acetate, benzyl cellulose and Hemophan, and mixtures thereof.

Examples of other materials include hydrophobic materials, such as aromatic polysulphones, polyethersulphones, polyetherether-sulphones, polyketones, polyetherketones and polyetherether-ketones, and sulphonated derivatives thereof, and mixtures thereof.

Examples of other materials include hydrophobic materials, such as polyesters, such as polycarbonates and polyamides, e.g. 6-6 and 6-10; polyacrylates, including, e.g. poly(methyl methacrylate), polyacrylonitrile and copolymers thereof, for example acrylonitrile—sodium metallosulphonate copolymers; and poly(vinylidene chloride).

Suitable materials for the present membranes include thermoplastic polyolefins, such as polyethylene e.g. high-density polyethylene, polypropylene, copolymers thereof, for example with vinyl acetate and polyvinyl alcohol, and mixtures thereof.

The dialysis membrane should have a molecular weight cut off (MWCO) chosen to allow selective perfusion of species deleterious to wound healing that have been targeted for removal from the wound. For example, perfusion of the serine protease elastase (molecular weight 25900 Dalton) would require a membrane with MWCO >25900 Dalton. The MWCO threshold can be varied to suit each application between 1 and 3000000 Dalton.

Preferably, the MWCO should be as close as possible to this weight to exclude interference by larger competitor species.

For example, such a membrane with MWCO >25900 Dalton does not allow any significant amounts of the antagonist to elastase, alpha-1-antitrypsin (AAT) (molecular weight 54000 Dalton), which occurs naturally in wounds, to diffuse freely out of the wound fluid into the dialysate. The inhibitor, which is beneficial in promoting chronic wound healing, remains in contact with the wound bed, and can act beneficially on it, whilst the elastase that is deleterious to wound healing is removed.

Such use of the present apparatus is, e.g. favourable to the wound healing process in chronic wounds, such as diabetic foot ulcers, and especially decubitus pressure ulcers.

As noted hereinafter, antagonists, for example degrading enzymes, or sequestrating agents for elastase on the dialysate side of the membrane, may be used to enhance the removal of this protease from wound exudate.

A less conventional type of two-phase system (see above) may be used as the means for fluid cleansing. In this type, the dialysis polymer film, sheet or membrane is not an integer selectively permeable to materials deleterious to wound healing, such as proteases, such as serine proteases, e.g. elastase, and thrombin; cysteine proteases; matrix metalloproteases, e.g. collagenase; and carboxyl (acid) proteases;

endotoxins, such as lipopolysaccharides;

inhibitors of angiogenesis such as thrombospondin-1 (TSP-1), plasminogen activator inhibitor, or angiostatin (plasminogen fragment)

pro-inflammatory cytokines such as tumour necrosis factor alpha (TNFα) and interleukin 1 beta (IL-1β);

oxidants, such as free radicals, e.g. , e.g. peroxide and superoxide; and metal ions, e.g. iron II and iron III; all involved in oxidative stress on the wound bed; and basic or acidic species which adversely affect the pH in the wound exudate, such as protons.

It will however also permit components of the exudate from a wound and/or irrigant fluid that may be larger or smaller molecules, but are beneficially involved in wound healing to pass into and through it.

In the dialysate, or preferably in one or more solid structural integers with at least one surface in contact with the dialysate, in the means for fluid cleansing, there are one or more materials that can remove materials deleterious to wound healing from wound exudate, by being antagonists to such species, for example enzymes or others, such as protease inhibitors, such as serine protease inhibitors, such as 4-(2-aminoethyl)-benzene sulphonyl fluoride (AEBSF, PefaBloc) and Nα-p-tosyl-L-lysine chloromethyl ketone (TLCK) and ε-aminocaproyl-p-chlorobenzylamide; cysteine protease inhibitors; matrix metalloprotease inhibitors; and carboxyl (acid) protease inhibitors;

binders and/or degraders, such as anti-inflammatory materials to bind or destroy lipopolysaccharides, e.g. peptidomimetics;

anti-oxidants, such as 3-hydroxytyramine (dopamine), ascorbic acid (vitamin C), vitamin E and glutathione, and stable derivatives thereof, and mixtures thereof; to relieve oxidative stress on the wound bed;

metal ion chelators and/or ion exchangers, such as transition metal ion chelators, such as iron III chelators (Fe III is involved in oxidative stress on the wound bed.), such as desferrioxamine (DFO), 3-hydroxytyramine (dopamine);

iron III reductants; and agents for the adjustment of pH in the wound exudate, such as base or acid scavengers and/or ion exchangers, or other species, which may be non-labile, insoluble and/or immobilised) species, such as ScavengePore® phenethyl morpholine (Aldrich).

They further include peptides (including cytokines, e.g. bacterial cytokines, such as α-amino-γ-butyrolactone and L-homocarnosine); and sacrificial redox materials that are potentially or actually beneficial in promoting wound healing, such as iron III reductants; and/or regeneratable materials of this type, such as glutathione redox systems; and other physiologically active components.

In use of the two-phase system dialysis unit, of this less conventional type, a broad spectrum of species will usually pass into the dialysate from the exudate.

Some (mainly ionic) species will pass from the dialysate into the irrigant and/or wound exudate through the dialysis polymer film, sheet or membrane that is not very selectively permeable to materials deleterious to wound healing.

The components of the exudate from a wound and/or irrigant fluid will diffuse freely to and fro through it.

A steady state concentration equilibrium is eventually set up between the dialysate and the irrigant and/or wound exudate, which is 'topped up' from the wound dressing.

Circulating wound fluid aids in the quicker attainment of this equilibrium of materials beneficial in promoting wound healing.

It also returns them to the site where they can be potentially of most benefit, i.e. the wound bed.

The target materials deleterious to wound healing also pass into the dialysate from the exudate through the dialysis polymer film, sheet or membrane that is not very selectively permeable to materials deleterious to wound healing.

Unlike the other components of the exudate from a wound and/or irrigant fluid, the target materials deleterious to wound healing come into contact with the dialysate, or preferably with one or more solid structural integers with at least one surface in the dialysate, and are removed by the appropriate antagonists, binders and/or degraders, chelators and/or ion exchangers and redox agents, etc. The cleansed fluid, still containing some materials that are beneficial in promoting wound healing, is returned to the wound.

Unlike the other components of the exudate from a wound and/or irrigant fluid the target materials are constantly removed from the dialysate, very little of these species will pass from the dialysate into the irrigant and/or wound exudate, and a steady state concentration equilibrium is not set up, even if the species are constantly 'topped up' from the wound dressing.

It is believed that circulating one or both fluids aids in removal from recirculation of the materials deleterious to wound healing from wound exudate, whilst retaining materials that are beneficial in promoting wound healing in contact with the wound.

A particular advantage of this form of the two-phase system, is that where a material that can remove materials deleterious to wound healing from wound exudate is (cyto) toxic or bioincompatible, or not inert to any components that are beneficial in promoting wound healing, the system does not allow any significant amounts of antagonist to diffuse freely out of the dialysate into the wound fluid. The active material can act beneficially on the fluid however.

The film sheet or membrane is preferably a dialysis membrane of molecular weight cut off (MWCO) (as conventionally defined) chosen to allow perfusion of species targeted for sequestration or destruction.

For example, sequestration of the serine protease elastase (molecular weight 25900 Dalton) would require a membrane with MWCO >25900 Dalton.

The MWCO threshold can be varied to suit each application between 1 and 3 000 000 Dalton. Preferably, the MWCO should be as close as possible to this weight to exclude sequestering interference by larger competitor species.

It will be seen that in many of the embodiments of the apparatus of this first aspect of the present invention for cleansing wounds, the irrigant and/or wound exudate and/or the cleansing fluid passes from the wound dressing and is returned via a return path to it, through or under the backing layer with a wound-facing face which is capable of forming a relatively fluid-tight seal or closure over a wound.

Each return path will require
at least one inlet pipe for connection to a fluid return tube, which passes through the wound-facing face of the backing layer, and
at least one outlet pipe for connection to a fluid offtake tube, which passes through the wound-facing face of the backing layer,
the point at which the or each inlet pipe and the or each outlet pipe passes through or under the wound-facing face forming a relatively fluid-tight seal or closure over the wound.

Where any pipe is described in connection with the operation of the apparatus as being connected or for connection to a (mating end of a) tube, the pipe and the tube may form a single integer.

Where the mode of running the present apparatus is in the form of a 'reversing system', the at least one inlet pipe and the at least one outlet pipe, and the at least one fluid supply tube and the at least one outlet pipe, may respectively be the same integer.

This is often in a 'multiple-pass system' for irrigant and/or wound exudate where this fluid passes from the wound dressing and is returned to the wound, in both cases via the cleansing means, e.g. under the action of the movement of a reciprocating pump, such as a syringe or piston pump.

The or each inlet pipe or outlet pipe may have the form of an aperture, such as a funnel, hole, opening, orifice, luer, slot or port for connection as a female member respectively to a mating end of a fluid return tube or a fluid offtake tube (optionally or as necessary via means for forming a tube, pipe or hose, or nozzle, as a male member.

Where the components are integral they will usually be made of the same material (for which it will be understood that materials that are listed above are amongst those that are suitable).

Where, alternatively, they are a push, snap or twist-lock fit, the may be of the same material or of different materials. In either case, materials that are listed above are amongst those that are suitable for all the components.

The backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound).

This is usually around each relevant tube, pipe or hose, or nozzle, hole, opening, orifice, luer, slot or port for connection to a mating end of a fluid return tube or fluid offtake tube.

Alternatively or additionally, where appropriate the backing layer may have a stiff flange or lip extending around the proximal face of the backing layer to stiffen, reinforce or otherwise strengthen the backing layer.

Both the single-phase system, such as an ultrafiltration unit, and two-phase system, such as a dialysis unit, may be in modular form that is relatively easily demountable from the apparatus of the invention.

Each return flow path (whether in a single-phase system or a two-phase system, such as an dialysis unit) requires a means for moving fluid.

Suitable means will be apparent to the skilled person, but the following types of small pump may be used as desired:
small reciprocating pumps, such as:
diaphragm pumps—where pulsations of one or two flexible diaphragms displace liquid while check valves control the direction of the fluid flow.

syringe and piston pumps—where pistons pump fluids optionally through check valves, in particular for variable and/or reversible positive and/or negative pressure on the wound bed and for closed single-phase reversing system, in which the wound exudate and/or irrigant passes to and fro through the cleansing means.

small rotary pumps, such as:

rotary vane pumps—with rotating vaned disk attached to a drive shaft moving fluid without pulsation as it spins. The outlet can be restricted without damaging the pump.

peristaltic pumps—with peripheral rollers on rotor arms acting on a flexible fluid circulation tube to urge fluid current flow in the tube in the direction of the rotor, in particular for a dialysate phase in a multiple-phase circulating system, in which it passes in only one direction.

The type and/or capacity of the device will be largely determined by the appropriate or desired fluid volume flow rate of irrigant and/or wound exudate from the wound for optimum performance of the wound healing process, and by factors such as portability, power consumption and isolation from contamination.

Such a device may also suitably be one that is capable of pulsed, continuous, variable, reversible and/or automated and/or programmable fluid movement. It may in particular be a pump of any of these types.

The main function of the invention, i.e. an apparatus, that is advantageously portable, for irrigating and/or cleansing wounds will largely determine the main function of the pump, i.e. a moving device for moving fluid, e.g. (chronic) wound exudate, through the cleansing means, rather than for aspirating or pressurising wounds that are being cleansed.

It may however be used to apply a positive or negative pressure of up to 50% atm., more usually up to 15% atm., to the wound, which may be pulsed, continuous, variable, reversible, automated and/or programmable, as for fluid movement.

A fluid-tight seal or closure of the wound dressing around the periphery of the backing layer then becomes more crucial, if wound cleansing is to be applied in this way.

The device is favourably a small peristaltic pump or diaphragm pump, e.g. preferably a miniature portable diaphragm or peristaltic pump. These are preferred types of pump, in order in particular to reduce or eliminate contact of internal surfaces and moving parts of the pump with (chronic) wound exudate, and for ease of cleaning.

Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as an electromechanical oscillator, a piezoelectric transducer, a core of a solenoid or a ferromagnetic integer and coil in which the direction of current flow alternates, a rotary cam and follower, and so on In one embodiment of the apparatus of this first aspect of the present invention for cleansing wounds with a two-phase system, such as one with a dialysis unit, no fluid passes from the wound dressing or is returned via a return path to it, through the backing layer.

It therefore does not require any inlet pipe for connection to a fluid return tube or any outlet pipe for connection to a fluid offtake tube, which passes through the wound-facing face of the backing layer.

In such an embodiment, the prime purpose of the moving device is to move the cleansing fluid. In such an embodiment, amongst suitable devices are:

Suitable examples of such a dressing include, e.g. those making use of rotary impellers, such as: vane impellers, with rotating vaned disk attached to a drive shaft, propellers on a drive shaft, etc.

Such devices may be integral with the dressing. It will be seen that the corresponding apparatus disadvantageously has a need to ensure a fluid-tight seal or closure of the chamber around any part of the moving device where it passes through the chamber wall or wound dressing. They may (disadvantageously) not be portable.

The possibility of using this type of wound dressing may be largely determined by the ability to achieve such a relatively fluid-tight seal or closure. It may be desirable that no part of the moving device pass through the chamber wall or wound dressing.

They may be separate structures, capable of interacting as appropriate for the purpose of moving cleansing fluid along a desired flow path across the selectively permeable integer, effectively in a 'multiple-pass system' within the interior of the chamber.

The moving device may drive the cleansing fluid inside the chamber remotely to set it in motion.

Such an embodiment of the apparatus advantageously enables a tight seal or closure over the wound, and no part of the moving device need pass through the chamber wall or wound dressing.

This avoids the need to ensure a fluid-tight seal or closure of the chamber around it.

The chamber may thus, e.g. be provided in a form with at least one magnetic follower enclosed within it and acted upon by a magnetic stirrer to impel the cleansing fluid. The magnetic stirrer to impel the cleansing fluid may be mounted on, e.g. releasably attached to the other components of the dressing, in particular the backing layer, e.g. with a Velcro™ attachment, an adhesive film (e.g. of pressure-sensitive adhesive) or elastic or non-elastic straps, bands, ties, bandages, e.g. compression bandages, sheets or covers, or be a push, snap or twist-lock fit with it/tem.

It may be mounted, e.g. centrally, on the backing layer above a circular or concentric toroidal hollow body that effectively forms an annular chamber provided with at least one magnetic follower within it. In use, the magnetic stirrer impels the magnetic follower enclosed within respectively the circular or the annular chamber to cause the wound cleansing fluid to circulate.

The film, sheet or membrane is often selectively permeable, contains the cleansing fluid, and should have the right resilience against the pulsing pressure to allow significant compression or decompression of the chamber to recirculate the wound cleansing fluid through it.

All such remote devices may be integral with or permanently attached to the dressing, in particular the backing layer, with an adhesive film, for example, or by heat-sealing.

These components may be releasably attached, e.g. by a Velcro™ attachment, with an adhesive film (e.g. with pressure-sensitive adhesive) or with elastic and non-elastic straps, bands, ties, bandages, e.g. compression bandages, sheets or covers.

Another such a device may be provided in the form of at least one ball or sphere, e.g. a solid metal ball or sphere.

This sets the cleansing fluid is in motion in contact with the surface of the integer that is selectively permeable to materials in the wound exudate under the action of the bodily movement of the patient.

Alternatively, the top of a compressible chamber may be provided with a trackway, around which the patient may run his or her fingers to move the fluid around the chamber.

In practice, even from a wound in a highly exuding state, such a rate of exudate flow is only of the order of up to 75 microliters/cm2/hr (where cm2 refers to the wound area), and the fluid can be highly mobile (owing to the proteases present).

Exudate levels drop and the consistency of wound exudate changes, e.g. to a higher viscosity liquid, as the wound heals, e.g. to a level for the same wound that equates to 12.5-25 microliters/cm2/hr.

Where materials deleterious to wound healing are removed by a two-phase system (See below.), such as a dialysis unit, fluid is also potentially lost to the system through the means for fluid cleansing.

This may occur, e.g. through a dialysis polymer film, sheet or membrane which is also permeable to water, in addition to materials deleterious to wound healing.

The balance of fluid in recirculation may thus further decrease. It may be desired to adjust the volume of the irrigant and/or wound exudate and hence to minimise this undesired loss.

If the consistency of wound exudate changes, e.g. to a higher viscosity liquid, as the wound heals, it may be desired to adjust the volume of the irrigant and/or wound exudate and hence to adjust the viscosity of the liquid, e.g. to a level that equates to the initial level.

As noted above, the apparatus of this first aspect of the present invention for cleansing wounds may be used with the wound space at atmospheric pressure or at a positive or negative pressure of up to 50% atm., more usually up to 15% atm. applied to the wound.

A fluid may be added to or removed from the wound space before and/or during wound therapy as may be desired to adjust the volume of the irrigant and/or wound exudate and/or to adjust the neutral, positive or negative pressure on the wound.

Thus, the volume of irrigant and/or wound exudate from the wound may be increased by continuing addition of irrigant to the wound space. A positive pressure may be applied to the wound by for example flooding it with a desired amount of irrigant before the dressing is applied to it and/or by continuing addition of irrigant to the wound during the run. A negative pressure may be applied to the wound by means of fluid removal from the wound, for example with a small pump.

This may be achieved in all cases by passage of the relevant fluid freely to and fro through a fluid regulator, such as a valve or other control device, e.g. a valve that is turned to switch between open and closed, that is mounted in a pipe or tube that passes through or under the backing layer.

For example, if exudate build-up under the backing layer becomes excessive during use, a bleed valve may be opened and excess fluid vented off, e.g. to a waste reservoir, and any excess pressure relieved.

Equally, any loss from any fluid from the wound may be adjusted, or a positive pressure (i.e. above-atmospheric pressure) may be applied to the wound bed by means of an irrigant which passes through a similar input regulator, such as a valve or other control device, e.g. a valve that is turned to switch between on and off, through or under the backing layer to the wound bed.

A negative pressure may be conveniently applied to the wound bed by means of fluid removal from the wound, for example with a small pump, through a similar vacuum regulator, such as a valve or other control device, e.g. a valve that is turned to closure once the vacuum has been applied, before disconnection of the vacuum source.

Alternatively or additionally, where appropriate the backing layer may have a regulator such as an injection septum, through which the desired amount of the relevant fluid, such as irrigant, may be removed from or supplied to the wound, for example with a small syringe or like pump to achieve the desired effect.

Equally, the balance in any cleansing fluid may be adjusted by means for bleeding or supplying fluid to the relevant flowpath. The means for bleeding or supplying fluid to the relevant flowpath may be situated in any appropriate part of the apparatus that is in contact with the cleansing fluid.

The means for bleeding or supplying fluid to the flowpath may be a regulator, such as a valve or other control device, e.g. a valve that is turned to switch between bleed and closure, for bleeding fluids from the apparatus, e.g. to a waste reservoir, such as a collection bag, or to switch between supply and closure, for supplying fluids to the apparatus.

Alternatively or additionally, where appropriate the flowpath may have a regulator such as an injection septum, through which the desired amount of the relevant fluid cleanser may be removed from or supplied to the flowpath, e.g. with a small syringe or like pump to achieve the desired effect.

The inlet and/or outlet pipes, the fluid return tube and the fluid offtake tube, etc. where present may be of conventional type, e.g. of elliptical or circular cross-section, and may suitably have a uniform cylindrical bore, channel, conduit or passage throughout their length.

Depending on the desired fluid volume flow rate of irrigant and/or wound exudate from the wound, and the desired amount in recirculation, suitably the largest cross-dimension of the bore may be up to 10 mm for large torso wounds, and up to 2 mm for limb wounds.

The tube walls should suitably thick enough to withstand any positive or negative pressure on them.

This is in particular the case if the volume of irrigant and/or wound exudate from the wound in recirculation is increased by continuing addition to it of wound exudate, and/or fluid passing from a cleansing fluid through a selectively permeable integer, for example the polymer film, sheet or membrane of a two-phase system, such as an dialysis unit. However, as noted above with regard to pumps, the prime purpose of such tubes is to convey irrigant and exudate through the length of the apparatus flow path, rather than to act as pressure vessels. The tube walls may suitably be at least 25 micron thick.

The whole length of the apparatus for aspirating, irrigating and/or cleansing wounds should be microbe-impermeable once the wound dressing is over the wound in use.

It is desirable that the wound dressing and the interior of the apparatus for aspirating, irrigating and/or cleansing wounds of the present invention is sterile.

The fluid may be sterilised in the system in which the fluid moves, including the means for fluid cleansing, by ultraviolet, gamma or electron beam irradiation. This way, in particular reduces or eliminates contact of internal surfaces and the fluid with any sterilising agent.

Examples of other methods of sterilisation of the fluid also include e.g. the use of ultrafiltration through microapertures or micropores, e.g. of 0.22 to 0.45 micron maximum cross-dimension, to be selectively impermeable to microbes; and fluid antiseptics, such as solutions of chemicals, such as chlorhexidine and povidone iodine; metal ion sources, such as silver salts, e.g. silver nitrate; and hydrogen peroxide;

although the latter involve contact of internal surfaces and the fluid with the sterilising agent.

It may be desirable that the interior of the wound dressing, the rest of the system in which the fluid recirculates, and/or the wound bed, even for a wound in a highly exuding state, are kept sterile, or that at least naturally occurring microbial growth is inhibited.

It is also desirable to provide a system in which physiologically active components of the exudate that are beneficial to wound healing are not removed before or after the application of fluid cleansing, e.g. by the passive deposition of materials that are beneficial in promoting wound healing, such as proteins, e.g. growth factors.

This may occur at any point in the system that is in contact with such physiologically active components of the exudate that are beneficial to wound healing.

Often this will occur at any point in the system that is in contact with the exudate, usually in a single-phase system, but it may occur in the second fluid (dialysate) phase in a multiple-phase system where materials in the wound exudate that are potentially beneficial to wound healing diffuse freely into that phase in use of the apparatus.

The deposition of materials that are beneficial in promoting wound healing may be combated by using a repellent coating at any point or on any integer in direct contact with the relevant fluid.

Examples of coating materials for surfaces over which the circulating fluid passes include anticoagulants, such as heparin, and high surface tension materials, such as PTFE, and polyamides, which are useful for growth factors, enzymes and other proteins and derivatives.

In all embodiments of the apparatus the type and material of any tubes throughout the apparatus of the invention for irrigating and/or cleansing wounds will be largely determined by their function.

To be suitable for use, in particular on chronic timescales, the material should be non-toxic and biocompatible, inert to any active components, as appropriate of the irrigant and/or wound exudate and of any dialysate. It should not allow any significant amounts of extractables to diffuse freely out of it in use of the apparatus.

It should be sterilisable by ultraviolet, gamma or electron beam irradiation and/or with fluid antiseptics, such as solutions of chemicals, fluid- and microbe-impermeable once in use, and flexible.

Examples of suitable materials include synthetic polymeric materials, such as polyolefins, such as polyethylene, e.g. high-density polyethylene and polypropylene.

Suitable materials for the present purpose also include copolymers thereof, for example with vinyl acetate and mixtures thereof. Suitable materials for the present purpose further include medical grade poly(vinyl chloride).

For the purposes of fluid cleansing in the apparatus of the present invention, both the single-phase system, such as an ultrafiltration unit, and two-phase system, such as a dialysis unit, may have captive (non-labile, insoluble and/or immobilised) species such as the following, bound to an insoluble and/or immobilised) substrate over and/or through which the irrigant and/or wound exudate from, the wound dressing passes in turn to the fluid return tube(s):

antioxidants and free radical scavengers, such as 3-hydroxytyramine (dopamine), ascorbic acid (vitamin C), vitamin E and glutathione, and stable derivatives thereof, and mixtures thereof; to relieve oxidative stress on the wound bed;

metal ion chelators and/or ion exchangers, such as transition metal ion chelators, such as iron III chelators (Fe III is involved in oxidative stress on the wound bed.), such as desferrioxamine (DFO), 3-hydroxytyramine (dopamine);

iron III reductants;

protease inhibitors, such as TIMPs and alpha 1-antitrypsin (AAT); serine protease inhibitors, such as 4-(2-aminoethyl)-benzene sulphonyl fluoride (AEBSF, PefaBloc) and N-α-p-tosyl-L-lysine chloro-methyl ketone (TLCK) and ε-aminocaproyl-p-chlorobenzylamide; cysteine protease inhibitors; matrix metalloprotease inhibitors; and carboxyl (acid) protease inhibitors;

sacrificial redox materials that are potentially or actually beneficial in promoting wound healing, by the removal of materials that trigger the expression into wound exudate of redox-sensitive genes that are deleterious to wound healing;

autoinducer signalling molecule degraders, which may be enzymes; and anti-inflammatory materials to bind or destroy lipopolysaccharides, e.g. peptidomimetics;

agents for the adjustment of pH in the wound exudate, such as base or acid scavengers and/or ion exchangers, or other species, which may be non-labile, insoluble and/or immobilised) species, such as ScavengePore® phenethyl morpholine (Aldrich).

Other physiologically active components of the exudate that are deleterious to wound healing may be removed in this way.

These may be removed with suitable chelators and/or ion exchangers, degraders, which may be enzymes, or other species.

The following types of functionalised substrate has sites on its surface that are capable of removing materials deleterious to wound healing on passing the circulating fluid from the wound over them:

heterogeneous resins , for example silica-supported reagents such as:

metal scavengers,
3-(diethylenetriamino)propyl-functionalised silica gel
2-(4-(ethylenediamino)benzene)ethyl-functionalised silica gel
3-(mercapto)propyl-functionalised silica gel
3-(1-thioureido)propyl-functionalised silica gel
triamine tetraacetate-functionalised silica gel
or electrophilic scavengers,
4-carboxybutyl-functionalised silica gel
4-ethyl benzenesulfonyl chloride-functionalised silica gel
propionyl chloride-functionalised silica gel
3-(isocyano)propyl-functionalised silica gel
3-(thiocyano)propyl-functionalised silica gel
3-(2-succinic anhydride)propyl-functionalised silica gel
3-(maleimido)propyl-functionalised silica gel
or nucleophilic scavengers,
3-aminopropyl-functionalised silica gel
3-(ethylenediamino)-functionalised silica gel
2-(4-(ethylenediamino)propyl-functionalised silica gel
3-(diethylenetriamino)propyl-functionalised silica gel
4-ethyl-benzenesulfonamide-functionalised silica gel
2-(4-toluenesulfonyl hydrazino)ethyl-functionalised silica gel
3-(mercapto)propyl-functionalised silica gel
dimethylsiloxy-functionalised silica gel
or base or acid scavengers,
3-(dimethylamino)propyl-functionalised silica gel
3-(1,3,4,6,7,8-hexahydro-2H-pyrimido-[1,2-α]pyrimidino)propyl-functionalised silica gel
3-(1-imidazol-1-yl)propyl-functionalised silica gel 3-(1-morpholino)propyl-functionalised silica gel
3-(1-piperazino)propyl-functionalised silica gel
3-(1-piperidino)propyl-functionalised silica gel
3-(4,4'-trimethyldipiperidino)propyl-functionalised silica gel
2-(2-pyridyl)ethyl-functionalised silica gel
3-(trimethylammonium)propyl-functionalised silica gel
or the reagents,
3-(1-cyclohexylcarbodiimido)propyl-functionalised silica gel
TEMPO-functionalised silica gel
2-(diphenylphosphino)ethyl-functionalised silica gel
2-(3,4-cyclohexyldiol)propyl-functionalised silica gel
3-(glycidoxy)propyl-functionalised silica gel
2-(3,4-epoxycyclohexyl)propyl-functionalised silica gel
1-(allyl)methyl-functionalised silica gel
4-bromopropyl-functionalised silica gel
4-bromophenyl-functionalised silica gel
3-chloropropyl-functionalised silica gel
4-benzyl chloride-functionalised silica gel
2-(carbomethoxy)propyl-functionalised silica gel
3-(4-nitrobenzamido)propyl-functionalised silica gel
3-(ureido)propyl-functionalised silica gel
or any combinations of the above.

The use of such captive (non-labile, insoluble and/or immobilised) species, such as the foregoing, bound to an insoluble and immobilised substrate over and/or through which the irrigant and/or wound exudate from, the wound dressing passes has been described hereinbefore as suitable for the means for fluid cleansing.

However, they may additionally, where appropriate, be used in any part of the apparatus that is in contact with the irrigant and/or wound exudate, but often within the dressing, for removal of materials deleterious to wound healing from wound.

In a second aspect of the present invention there is provided a method of treating wounds to promote wound healing using the apparatus for cleansing wounds of the present invention.

BRIEF DESCRIPTION OF THE DRAWINGS

The present invention will now be described by way of example only with reference to the accompanying drawings in which:

FIGS. 1 to 11 and 14 show apparatus with a single-phase means for wound exudate cleansing, and of these:

FIGS. 1, 2, 3, 6 7 and 14 show a reversing system, in which the wound exudate and optionally irrigant passes through the cleansing means one or more times at least once in opposing directions; and FIGS. 2, 4, 5, 8, 9, 11 and 15 show a circulating system, in which it/they pass in only one direction; and FIGS. 12 and 13 show apparatus with a two-phase means for wound exudate cleansing, and of these:

FIGS. 12 and 13 show such apparatus in which the cleansing phase passes through the cleansing means.

DETAILED DESCRIPTION OF THE PREFERRED EMBODIMENT

Figure 1:
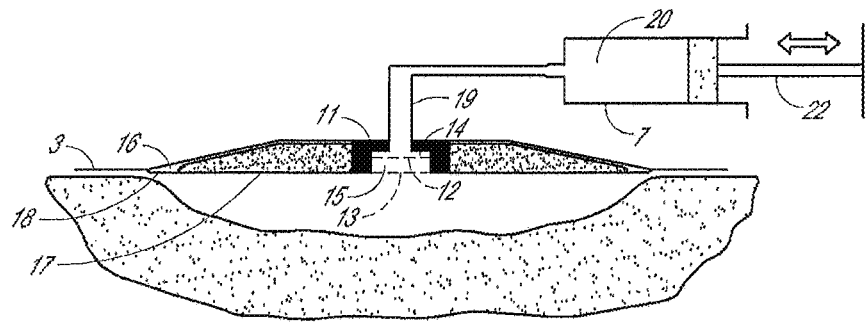
FIGS. 1 to 15 are cross-sectional views of apparatus for cleansing a wound according to the first aspect of the present invention.

Referring to FIGS. 1 to 10 and 14, the apparatus (1) for cleansing wounds comprises a conformable wound dressing (2), having a backing layer (3) which is capable of forming a relatively fluid-tight seal or closure over a wound and bears an adhesive film, to attach it to the skin sufficiently to hold the wound dressing (2) in place;

a cleansing means (4) for selectively removing materials that are deleterious to wound healing from wound exudate, which means is under the backing layer (3) and sits in the underlying wound in use; and a moving device (7) for moving fluid through the cleansing means.

Optional means for bleeding or supplying fluid to the cleansing means (4) or to exudate under the backing layer, e.g. a regulator, such as a valve are omitted in most of the Figures.

In FIG. 1, a reversing system is shown (wound exudate passes through the cleansing means at least once in opposing directions).

The microbe-impermeable film backing layer (3) bears a centrally attached proximally projecting recessed boss (11).

A porous film (12) and a permeable membrane (13) mounted in the recess (14) of the boss (11) define a cleansing chamber (15), which contains a solid particulate (not shown) for sequestering deleterious materials from, but initially separated from the wound exudate. These integers form the cleansing means (4).

An annular chamber (16) about the boss (11) is defined by a fluid-impermeable film (17) that extends between and is attached to the boss (11) and the underside of the backing layer (3). It is filled with a flexibly resilient foam (18)

An inlet and outlet pipe (19) passes centrally through the boss (11) and communicates between the interior of the boss (11) and a syringe barrel (20), which is part of a syringe moving device (7).

In use, movement of the syringe plunger (22) sucks and forces wound exudate to and fro through the cleansing means (4).

Figure 2:
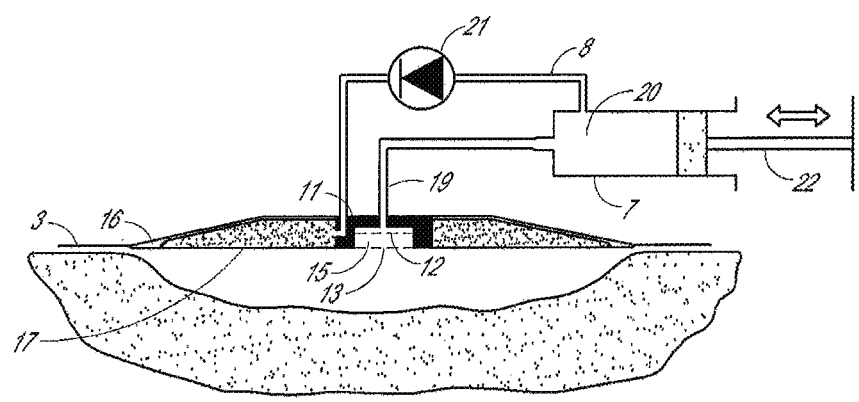

The apparatus (1) in FIG. 2 may be operated as a circulating system or as both a circulating system and as a reversing system.

It is similar in construction to FIG. 1, but differs mainly in that an inlet pipe return loop (19) passes in a bend through the boss (11) and communicates between the interior of the chamber (16) and the syringe barrel (20) via a non-return valve (21), the resistance of which to flow is low relative to the resistance of the cleansing means (4). Means for bleeding fluid from the chamber (16), such as a valve, is omitted from FIG. 2.

In use, the plunger (22) of the syringe moving device (7) is withdrawn to suck wound exudate into the cleansing means (4), which sequesters deleterious materials from the wound exudate.

The plunger (22) of the syringe moving device (7) is then returned to force cleansed wound exudate through the valve (21) into the annular chamber (16), and thence through the porous film (17) back into the wound.

A proportion of cleansed wound exudate is also pushed back through the cleansing means (4) at each return stroke of the syringe plunger. The proportion will depend largely on the position of the return loop (19) on the syringe barrel. The amount pumped to the annular chamber (16) will decrease the further from the proximal end of the syringe the return loop links to the syringe barrel, as the plunger cuts off the return loop (19) in the later part of the return stroke.

Depending largely on the type of cleansing means that is employed in this embodiment of the apparatus of the present invention, the resistance of the valve (21) relative to the resistance of the cleansing means (4) may also affect the proportion through the chamber (16) and through the porous film (17).

Excess pressure in the chamber (16), e.g. from wound exudate from a wound in a highly exuding state, may be relieved by a bleed valve, if fitted.

Figure 3:
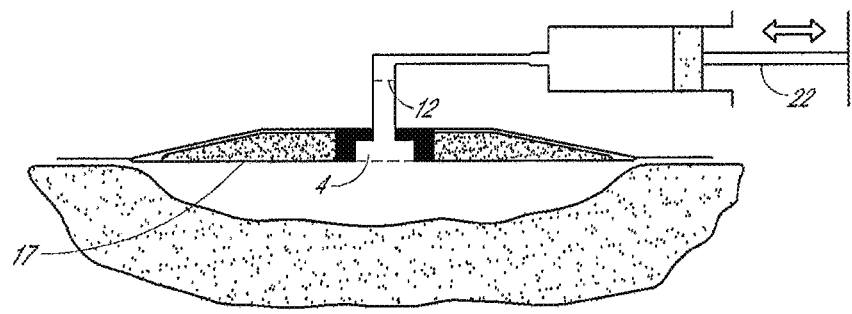

The apparatus (1) in FIG. 3 differs mainly from that in FIG. 2 in the position of the porous film (12) in the flow path.

The mode of use is the same: movement of the syringe plunger (22) sucks and forces wound exudate to and from through the cleansing means (4).

Figure 4A:
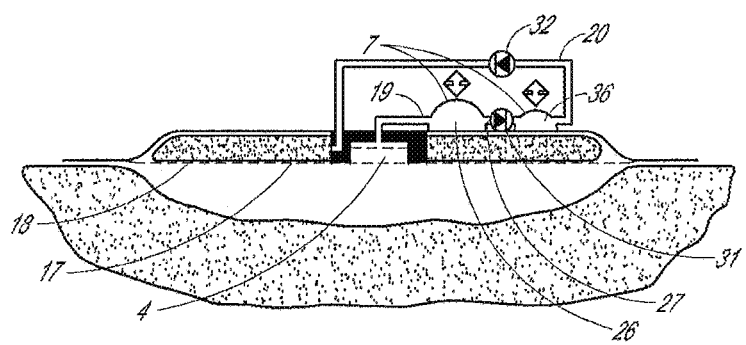
Figure 4B:
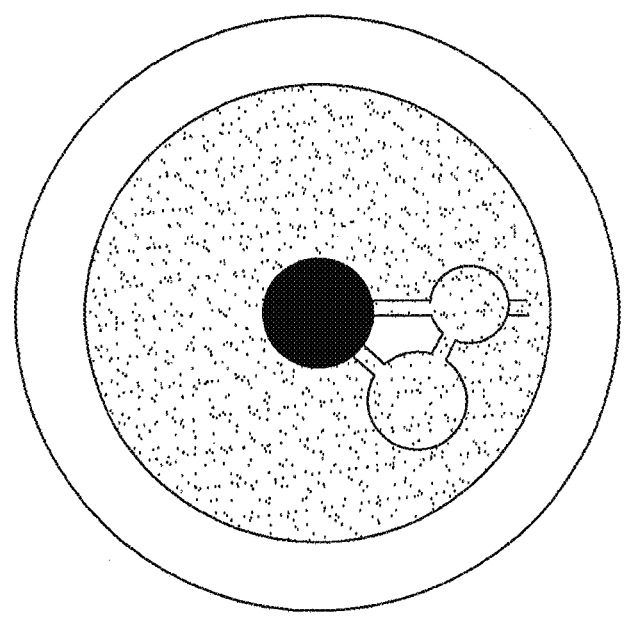

The apparatus (1) in FIG. 4 differs from that in FIG. 2 in the moving device (7).

This is a press-button pump in place of a syringe. The pump (7) is mounted on the distal face of the backing layer (3).

It comprises a resiliently compressible intake chamber (26), connected by an outlet pipe (19) to the cleansing means (4) and by a transfer tube (27) via a low resistance first non-return valve (31) to a resiliently compressible output chamber (36), connected via an inlet pipe (20) and a low resistance second non-return valve (32) to the interior of the chamber (16).

In use, the intake chamber (26) is manually compressed and released, its return to its original configuration causing wound exudate to be drawn through the cleansing means (4).

The output chamber (36) is then manually compressed and released, its return to its original configuration causing cleansed wound exudate to be drawn through the first non-return valve (31) from the intake chamber (26).

The intake chamber (26) is then manually compressed again and released, its compression causing cleansed wound exudate to be pumped into the output chamber (36) through the first non-return valve (31) from the intake chamber (26), and its return to its original configuration causing wound exudate to be drawn through the cleansing means (4).

The output chamber (36) is then manually compressed again and released, its compression causing cleansed wound exudate to be pumped into the chamber (16) through the second non-return valve (32) from the output chamber (36), and its return to its original configuration causing cleansed wound exudate to be drawn through the intake chamber (26).

The cycle is repeated as long as desired, and from the second cycle onwards, when the output chamber (36) is manually compressed, it causes cleansed wound exudate to be forced through the annular chamber (16), and thence through the porous film (17) back into the wound.

Referring to FIGS. 5 to 7 and 10, the apparatus (1) in each comprises a cleansing means (4), which comprises a chamber (5), here a conformable hollow bag, defined by the backing layer (3) and a polymer film (6) that is permeable and permanently attached to the proximal face of the backing layer (3).

It sits under the domed backing layer (3) in the underlying wound in use, and contains a cleansing fluid absorbed in a resiliently flexible foam (41).

FIGS. 5 to 7 and 10 show different methods of moving wound exudate in and out of the cleansing means (4).

Figure 5:
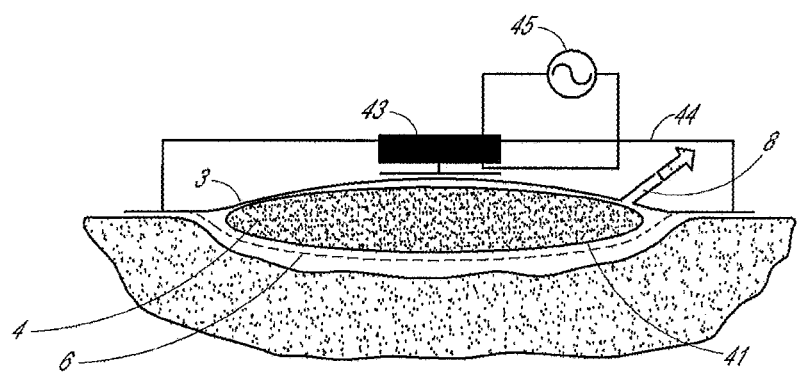

In FIG. 5, an electromechanical oscillator or piezoelectric transducer (43) is mounted centrally in contact with the backing layer (3) on a rigid frame (44) mounted at the periphery of the backing layer (3), and is connected electrically to an appropriate alternating electrical power source (45) (shown schematically). The chamber (5) is provided with a bleed valve (8).

If exudate build up under the backing layer (3) becomes excessive during use, the bleed valve (8) may be opened and excess fluid vented off, and any excess pressure relieved.

Figure 6:
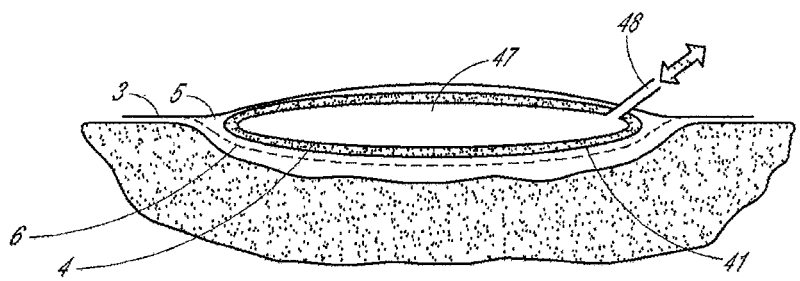

In FIG. 6, the foam (41) has a resiliently flexible, balloon core (47), which is inflatable and deflatable with a fluid, such as a gas, e.g. air or nitrogen, or a liquid, such as water or saline, to apply varying pressure to the chamber (5) via an inlet and outlet pipe (48) mounted at the periphery of the backing layer (3).

The pipe (48) is connected to a suitable moving device (58) (not shown) for moving the inflating fluid in and out of the core (47) and thus to move wound exudate in and out of the cleansing means (4). Such a device is suitably one that is capable of optionally pulsed, reversible fluid movement.

It may in particular be a small peristaltic pump or diaphragm pump, e.g. preferably a battery-driven miniature portable diaphragm or peristaltic pump, e.g. mounted centrally on the backing layer (3) above the chamber (5) and is releasably attached to the backing layer (3).

Figure 7:
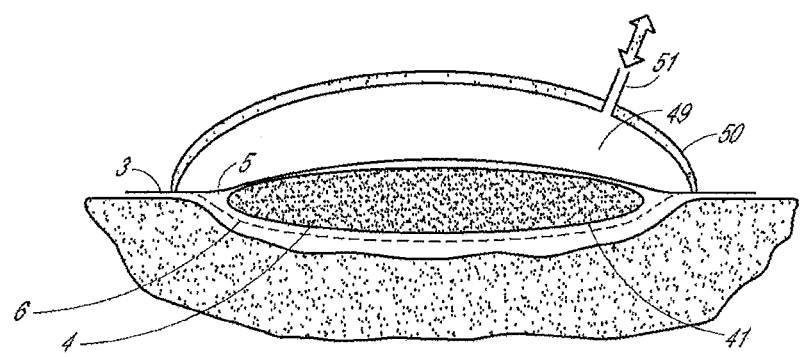

FIG. 7 shows a variant of the apparatus (1) of FIG. 6. The resiliently flexible, balloon core (47) under the backing layer (3) is replaced by a resiliently flexible, balloon chamber (49), defined by the backing layer (3) and a rigid polymer dome (50) that is impermeable and permanently attached to the distal face of the backing layer (3).

The balloon chamber (49), defined by the backing layer (3) and the rigid polymer dome (50) is also inflatable and deflatable with a fluid, such as a gas, e.g. air or nitrogen, or a liquid, such as water or saline, to apply varying pressure to the chamber (5) via an inlet and outlet pipe (51) mounted at the periphery of the backing dome (50).

A suitable moving device (58) (not shown) is used for moving the inflating fluid in and out of the balloon chamber (49) and thus to move wound exudate in and out of the cleansing means (4), as noted in respect of FIG. 6, and may be mounted on the dome (50) rather than the backing layer (3).

Figure 10:
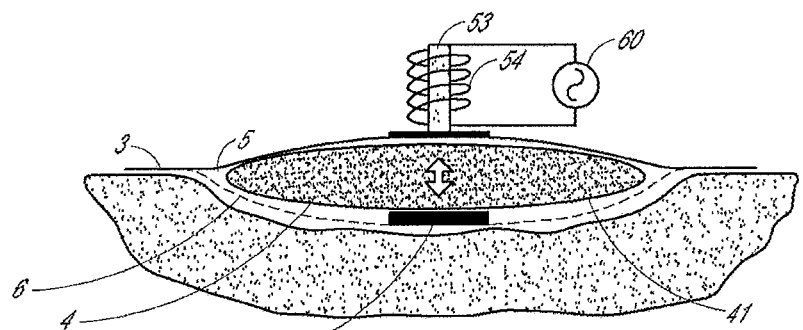

In FIG. 10, an electromagnetic solenoid core (53) within an electrical coil (54) is mounted centrally in contact with the backing layer (3) on a rigid flange (55). The electrical coil (54) is connected electrically to an appropriate alternating electrical power source (60) (shown schematically).

The chamber (5) is provided at its base with an attached disc (56) of a ferromagnetic material sheathed from the wound exudate and cleansing fluid.

As the direction of current flow alternates, the solenoid core follows, and so compresses and releases the chamber (5), and hence causes wound exudate to be forced to and fro through the cleansing means (4).

Figure 8:
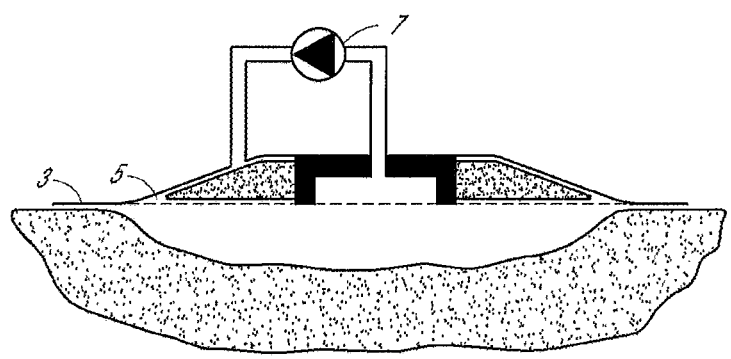
Figure 9:
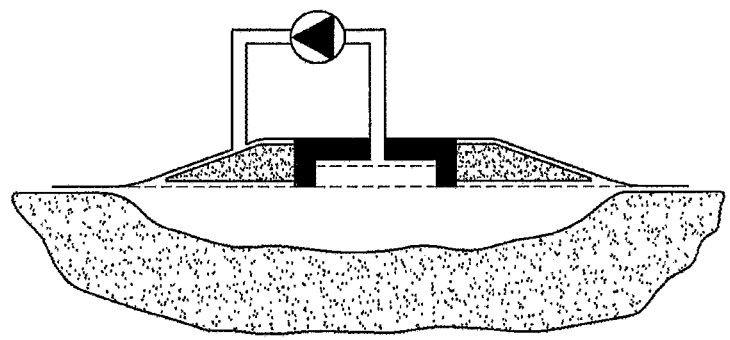

FIGS. 8 and 9 show a variant of the apparatus (1) of FIGS. 1 and 4. The moving device (7) in both cases that respectively replaces the syringe and the press-button pump is a small peristaltic pump or diaphragm pump.

It is preferably a battery-driven miniature portable diaphragm or peristaltic pump, e.g. mounted centrally on the backing layer (3) above the chamber (5) and is releasably attached to the backing layer (3).

Figure 11:
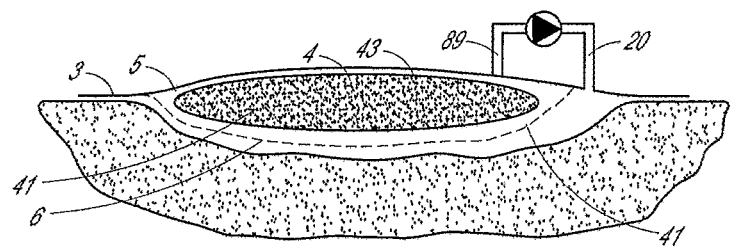

FIG. 11 shows apparatus with a single-phase means for wound exudate cleansing in which the wound exudate passes through the cleansing means one or more times in only one direction. It is similar in structure to the apparatus shown in FIGS. 5 to 7 and 10.

The apparatus (1) comprises a cleansing means (4), which comprises a chamber (5), here a conformable hollow bag, defined by the backing layer (3) and a polymer film (6) that is permeable and permanently attached to the proximal face of the backing layer (3). It contains a cleansing fluid absorbed in a resiliently flexible foam (41).

The resiliently flexible foam (41) is contained in a permeable membrane (43) and contains a material for sequestering deleterious materials from the wound exudate.

These integers form the cleansing means (4).

An outlet pipe (69) passes centrally through the backing layer (3) and communicates between the interior of the chamber (5) and a pump, e.g. preferably a battery-driven miniature portable diaphragm or peristaltic pump, e.g. mounted centrally on the backing layer (3) above the chamber (5) and releasably attached to the backing layer (3).

An inlet pipe (20) passes peripherally through the backing layer (3) and communicates between the wound space and the pump.

In use, wound exudate is moved by the pump (7) through the cleansing means (4), and the foam (41) sequesters deleterious materials from the wound exudate.

FIG. 12 shows apparatus with a two-phase means for wound exudate cleansing in which the cleansing phase moves.

Figure 12A:
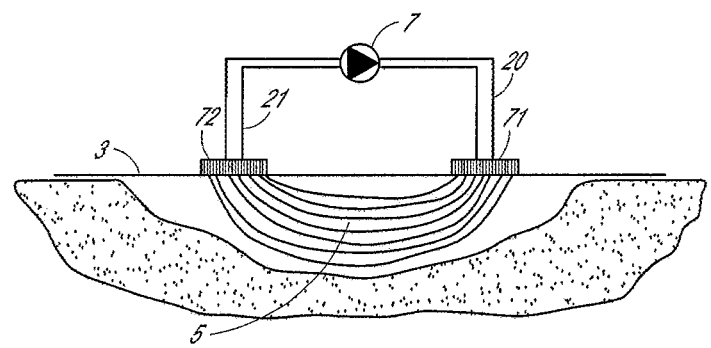

FIG. 12a shows apparatus in which the only the cleansing phase moves.

Figure 12B:
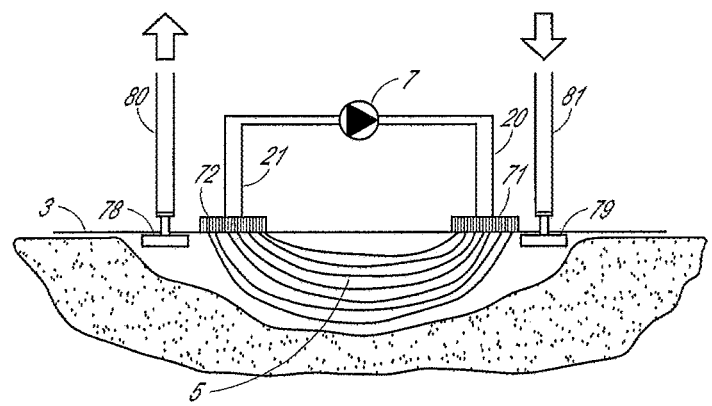

FIG. 12b shows apparatus in which the cleansing phase and the wound exudate phase move.

In both Figures, the apparatus (1) comprises a cleansing means (4), which comprises a chamber (5), here in the form of tubules in an array under the backing layer (3) between a first boss (71) and a second boss (72) both mounted in the backing layer (3). The tubules are made from a polymer membrane that is selectively permeable to deleterious materials in the wound exudate, and contain a dialysate fluid.

An inlet pipe (20) passes from the first boss (71) and communicates between the interior of the chamber (5) and a pump (7), e.g. preferably a battery-driven miniature portable diaphragm or peristaltic pump, e.g. mounted centrally on the backing layer (3) above the chamber (5) and releasably attached to the backing layer (3). An outlet pipe (21) passes from the second boss (72) and communicates between the interior of the chamber (5) and the pump (7).

In use, dialysate fluid is moved by the pump (7) through the cleansing means (4), and it removes deleterious materials from the wound exudate.

In FIG. 12b, a third boss (78) with a wound exudate outlet passing centrally through it and a fourth boss (79) with a wound exudate inlet passing centrally through it are both mounted peripherally and mutually diametrically opposed in the backing layer (3).

A wound exudate outlet tube (80) is connected to the third boss (78) and communicates between the interior of the wound and the inlet of a second pump (82) (not shown), e.g. preferably a battery-driven miniature portable diaphragm or peristaltic pump, mounted centrally on the backing layer (3).

A wound exudate inlet tube (81) is connected to the fourth boss (79) and communicates between the interior of the wound and the outlet of the second pump.

In use, not only is dialysate fluid moved by the first pump (7) through the cleansing means (4), where it removes deleterious materials from the wound exudate, but the wound exudate phase is moved under the backing layer (3) through the wound space by the second pump in a countercurrent direction to enhance the removal from the wound exudate.

Figure 13:
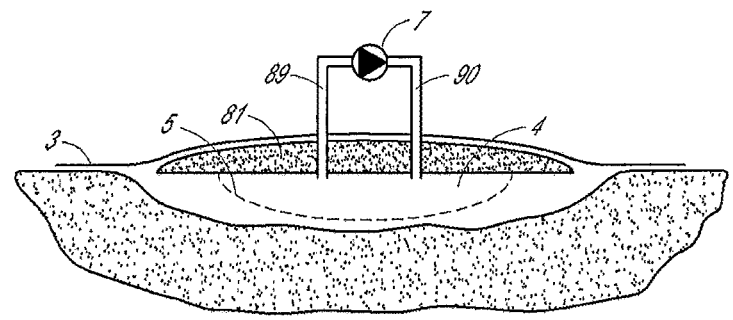

FIG. 13 shows apparatus with a two-phase means for wound exudate cleansing in which the cleansing phase moves.

The apparatus (1) comprises a cleansing means (4), which comprises a chamber (5), here in the form of bag under the backing layer (3) and under a foam filler (81).

This bag is made from a polymer membrane and contains a dialysate fluid, which contains a material as a solute or disperse phase species that is for sequestering or degrading deleterious materials from the wound exudate. The membrane is chosen to be selectively permeable to allow perfusion of deleterious material species targeted for sequestration or destruction from the wound exudate into the dialysate, but not to allow any significant amounts of antagonist in the dialysate fluid phase to diffuse freely out of the dialysate into the wound fluid.

An outlet pipe (89) passes through the backing layer (3) and communicates between the interior of the chamber (5) and a pump, e.g. preferably a battery-driven miniature portable diaphragm or peristaltic pump, e.g. mounted centrally on the backing layer (3) above the chamber (5) and releasably attached to the backing layer (3). An inlet pipe (90) passes peripherally through the backing layer (3) and communicates between the chamber (5) and the pump.

In use, dialysate is moved by the pump (7) through the cleansing means (4). Deleterious material species targeted for sequestration or destruction from the wound exudate into the dialysate, where the antagonist in the dialysate fluid phase removes deleterious materials from the wound exudate, without diffusing out into the exudate.

Figure 14:
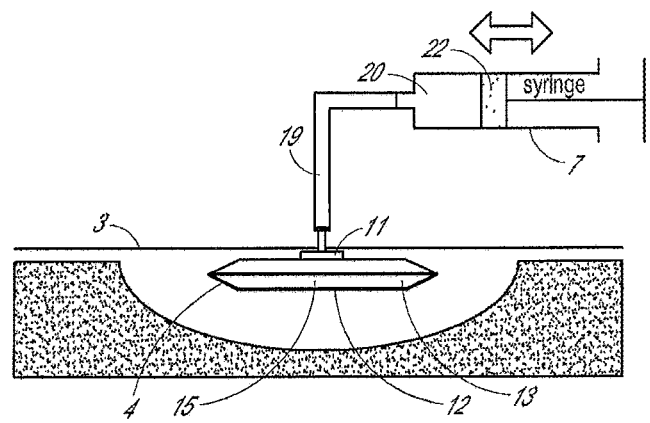

In FIG. 14, a reversing system is shown (wound exudate passes through the cleansing means at least once in opposing directions) that is similar in structure to the apparatus shown in FIGS. 1 and 3.

The microbe-impermeable polyurethane film backing layer (3), formed by solution casting or extrusion, bears a centrally attached proximally projecting boss (11) with a luer for connection to a mating end of a fluid supply and offtake tube (19), which communicates between the interior of the boss (11) and a syringe barrel (20), which is part of a syringe moving device (7).

A lower porous film (12) and an intermediate porous membrane (13), both made of permeable polyurethane membrane with small apertures or pores, define a cleansing chamber (15), which contains a solid particulate (not shown).

This is for sequestering deleterious materials from, but initially separated from, the wound exudate. These integers, with a coextensive impermeable upper sheet (24) with an upper aperture adapted to register with the conduit in the boss (11), form an upper chamber (25), and all together form the cleansing means (4). This is mounted on the lower face of the boss (11) with the upper aperture in register with the conduit in the boss (11).

In use, movement of the syringe plunger (22) sucks and forces wound exudate to and fro through the cleansing means (4).

Figure 15:
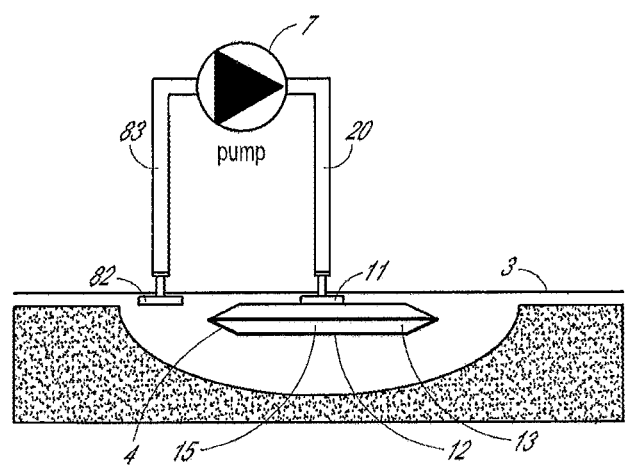

The apparatus (1) in FIG. 15 is a circulating system (wound exudate passes through the cleansing means one or more times in only one direction). It is a variant of the apparatus (1) of FIGS. 8 and 9.

The microbe-impermeable polyurethane film backing layer (3), formed by solution casting, bears a centrally mounted proximally projecting boss (11) with a uniform cylindrical-bore conduit through it and a luer for connection to a mating end of a fluid supply tube (20), which communicates between the interior of the boss (11) and the outlet of moving device (7).

The moving device (7) is a battery-driven miniature portable diaphragm or peristaltic pump, mounted centrally on the backing layer (3) and is releasably attached to the backing layer (3).

A second proximally projecting boss (82) with a luer for connection to a mating end of a fluid offtake tube (83) is mounted peripherally on the backing layer (3). The fluid offtake tube (83) communicates between the wound space and the inlet of the pump (7).

A lower porous film (12) and an intermediate porous membrane (13), both made of permeable polyurethane membrane with small apertures or pores, define a cleansing chamber (15), which contains a solid particulate (not shown) for sequestering deleterious materials from, but initially separated from, the wound exudate. These integers, with a coextensive impermeable upper sheet (24) with an upper aperture adapted to register with the conduit in the boss (11), form an upper chamber (25), and all together form the cleansing means (4).

This is mounted on the lower face of the boss (11) with the upper aperture in register with the conduit in the boss (11).

In use, wound exudate is moved by the pump (7) through the cleansing means (4), and the particulate (not shown) sequesters deleterious materials from the wound exudate The use of the apparatus of the present invention will now be described by way of example only in the following Examples:

EXAMPLE 1

Cleansing Fe(II) from Aqueous Solution with the Apparatus of FIG. 1: Single-Phase Hand-Syringe Pumped Dressing Containing Solid Sequestrant (Cadexomer-desferrioxamine)

A hand-syringe pumped dressing as shown in FIG. 14 was made up. The cleansing chamber (15) contains a solid particulate (not shown) desferrioxamine supported on Cadexomer (50 mg) to sequester and remove deleterious Fe(II) ions from surrogate exudate.

The porous film (12) and a permeable membrane (13), both made of Porvair permeable membrane, are chosen to allow perfusion and flow under syringe pumping through the cleanser but to contain the solid reagent.

In triplicate, the dressing as shown in FIG. 1 was applied to a 9.60 ml capacity circular wound cavity (cast in Perspex) containing an aqueous solution of ferrous chloride tetrahydrate (Aldrich) (9.60 ml, 200 μmolar).

The solution was repeatedly completely withdrawn and completely reinjected using the device syringe. At each withdrawal, a 100 microliter aliquot of solution was assayed using a ferrozine assay as follows: each 100 ul aliquot was added immediately to a 1.5 ml capacity, 1 cm path-length UV cuvette containing 1 ml Ferrozine stock solution (73.93 mg Ferrozine was made up to 250 ml in distilled water (600 uM)). Absorbance (562 nm) readings were taken after at least 5 min. incubation. The absorbance was measured using UNICAM UV4-100 UV-Vis spectrophotometer V3.32 (serial no. 022405).

Six passes were made in total, at four minute intervals. The same method was repeated in the absence of flow (i.e. without syringe pumping through the cleanser) and sampled at equivalent time points.
Results and Conclusions The resulting iron concentration profiles were averaged and the standard deviations were determined. The Fe(II) concentration is effectively depleted to background level in 3 full cycles (12 minutes). In the control, insignificant concentration change has occurred in the same time period. The dressing as shown in FIG. 1 effectively sequesters Fe(II) from aqueous solution such as water, saline or wound exudate.

EXAMPLE 2

Neutralising the pH of an Acidic Solution with the Apparatus of FIG. 15: Single-Phase Recirculating Pumped Dressing Containing Solid Acid Scavenger, ScavengePore® Phenethyl Morpholine A recirculating pumped dressing as shown in FIG. 15 was made up. The cleansing chamber (15) contains a solid particulate (not shown) of ScavengePore® phenethyl morpholine (Aldrich) (50 mg), which is a low-swelling macroporous highly crosslinked polystyrene/divinylbenzene ion-exchanger resin matrix, with 200-400 micron particle size, to scavenge and remove protons, which are acidic species which adversely affect the pH in the wound exudate, from surrogate exudate.

The porous film (12) and a permeable membrane (13), both made of Porvair permeable membrane, are chosen to allow perfusion and flow under pumping through the cleanser but to contain the ion-exchange reagent.

In triplicate, 4.80 ml DMEM was In triplicate, Device 2 was applied to a 9.60 ml capacity circular wound cavity (cast in Perspex) containing Dulbecco's Modified Eagles Medium (DMEM) (Sigma) (4.80 ml, pH adjusted to pH 6.6 using hydrochloric acid (0.975 N in water, 75 μl). The remaining cavity volume was filled with glass beads. The solution was circulated through the cavity at a flow rate of 2.35 ml min-1.

100 μl samples were taken at 5 min. time points up to 40 min, and pH was recorded using a flat-bed pH meter. The same method was repeated in the absence of flow (i.e. no pump circulation of the solution) and sampled at equivalent time points.
Results and Conclusions The resulting pH profiles were averaged and standard deviations determined. The pH was effectively adjusted to pH 7.4 in 40 min. In the control, a slower change in pH was observed in the same time period to pH 7.

EXAMPLE 3

Cleansing Elastase from Aqueous Solution by Diffusion Across a Dialysis Membrane with the Apparatus of FIG. 12: Two-Phase Recirculating Pumped Dressing Containing No Reagent A recirculating pumped dressing as shown in FIG. 12 was made up. The cleansing chamber (5) is in the form of tubules made from a polymer membrane that is selectively permeable to a deleterious materials in wound exudate (elastase). These in an array under the backing layer (3) within the wound space between a first boss (71) and a second boss (72) both mounted in the backing layer (3). The tubules contain a dialysate fluid and are in a circuit with a pump (7).

In triplicate, the dressing as shown in FIG. 12 was applied to a 9.60 ml capacity circular wound cavity (cast in Perspex) containing elastase solution (porcine pancreatic elastase, Sigma) (4.80 ml, 0.5 mgml-1 in TRIS buffer, pH 8.2, 0.2 M). The remaining cavity volume was filled with glass beads. The inlet and outlet ports were connected to the circulating pump.

The dialysate system was prefilled with TRIS (pH 8.0, 0.2 M). This was circulated through the dressing at a flow rate of 2.35 ml min-1. 10 μl samples of the circulating solution were taken at 5 min. time points up to 45 min, and the activity was recorded using a standard N-succinyl-(ala)3-p-nitroanilide colorimetric assay. The same method was repeated in the absence of flow (i.e. no pump circulation of the solution) and sampled at equivalent time points.

Results and Conclusions

The activity of the samples was determined from their absorbances at 405 nm using a UV/Vis spectrometer. Results were averaged and standard deviations determined. Effective transfer of elastase across the dialysis membrane is seen in 45 min. In the control, no effective transfer was observed in the same time period.

EXAMPLE 4

Cleansing Fe(II) from Aqueous Solution with the Apparatus of FIG. 13: Two-Phase Recirculating Pumped Dressing Containing Liquid Phase Sequestrant (Starch—desferrioxamine (DFO) Conjugate)

An analogue of the apparatus (1) in FIG. 13 was made up, i.e. with a circulating system (wound exudate passes through the cleansing means one or more times in only one direction) with a two-phase means for wound exudate cleansing in which the cleansing phase moves.

The apparatus (1) comprises a cleansing means (4), which comprises a chamber (5) which is made from a polymer membrane and contains a dialysate fluid, which contains a material as a solute or disperse phase species that is for sequestering or degrading deleterious materials from the wound exudate.

The membrane is chosen to be selectively permeable to allow perfusion of deleterious material species targeted for sequestration or destruction from the wound exudate into the dialysate, but not to allow any significant amounts of antagonist in the dialysate fluid phase to diffuse freely out of the dialysate into the wound fluid.

The analogue is a circuit containing a 0.5-1.0 ml capacity Slide-A-Lyzer dialysis unit, with an upper chamber and a lower chamber in which wound exudate and cleansing fluid respectively are separated from each other by a polymer membrane chosen to have the properties noted above (MWCO 10000).

The lower chamber, through which cleansing fluid passes, has diagonally opposed inlet and outlet ports, which are opened with needles, connected to a circuit of 5 ml capacity containing a dialysate reservoir and a battery-driven miniature portable diaphragm or peristaltic pump. The circuit contains an aqueous high molecular weight starch—DFO conjugate (5 ml, 4 mg/ml).

An aliquot of ferrous chloride tetrahydrate (Aldrich) solution (0.5 ml 3 mM) was placed in the upper cavity of the slide and dialysed with 3.6 ml/min. flow in the circuit and (as a control) in the absence of flow in the circuit.

10 microliter aliquots were removed for 30 minutes at 5 minutes intervals (including t=0). The 10 microliter aliquot of solution was assayed using the ferrozine iron(II) determination assay as described in Example 1 above. These experiments were performed in triplicate.

Results and Conclusions

The resulting iron concentration profiles were averaged and standard deviations determined. The Fe(II) concentration was effectively depleted to approximately 50% of the initial level in 30 minutes. Without circuit flow, Fe(II) concentration was depleted to approximately 75% of the starting value in the same time period. The apparatus effectively sequesters Fe(II) from aqueous solution.

What is claimed is:

1. A negative pressure wound therapy system, comprising:
   a wound dressing comprising:
      a backing layer comprising an opening and a proximal, wound-facing face and a distal face;
      a lower permeable layer configured to contact a wound; and
      a chamber between the backing layer and the lower permeable layer; and
      a resiliently flexible filler positioned within the chamber, the resiliently flexible filler comprising an absorbent material configured to retain wound exudate within the chamber;
   a fluid outlet conduit configured to provide fluid communication between a negative pressure source and the wound dressing, the fluid outlet conduit being in fluid communication with the chamber of the wound dressing; and
   a connector attached to the backing layer and forming a seal around the opening in the backing layer, wherein the connector is configured to connect the fluid outlet conduit to the wound dressing; and
   a porous material positioned in the flow path between the chamber and the negative pressure source and configured to prevent passage of the wound exudate from the chamber into the fluid outlet conduit.

2. The system of claim 1, wherein the chamber is defined between the backing layer and the lower permeable layer.

3. The system of claim 1, wherein the wound dressing further comprises an adhesive film positioned underneath a periphery of the wound-facing face of the backing layer, the adhesive film configured to attach the wound dressing to skin around the wound.

4. The system of claim 1, further comprising an upper permeable layer above the resiliently flexible filler and underneath the backing layer, the upper permeable layer at least partially containing the resiliently flexible filler.

5. The system of claim 4, further comprising a foam layer above the upper permeable layer and underneath the backing layer.

6. The system of claim 1, wherein the lower permeable layer is attached to the backing layer.

7. The system of claim 1, wherein the lower permeable layer, the resiliently flexible filler and the backing layer are integral with each other.

8. The system of claim 1, wherein the absorbent material is configured to selectively remove the wound exudate.

9. The system of claim 1, wherein the wound dressing is configured to absorb wound exudate within a gel within the filler upon application of negative pressure to the wound dressing.

10. The system of claim 9, wherein the resiliently flexible filler comprises a cellulosic material.

11. The system of claim 1, further comprising a negative pressure source configured to apply negative pressure to the wound dressing through the fluid outlet conduit.

12. The system of claim 11, wherein the negative pressure source comprises a battery-driven pump.

13. The system of claim 12, wherein the negative pressure source comprises a diaphragm pump.

14. The system of claim 12, wherein the negative pressure source comprises a peristaltic pump.

15. The system of claim 1, wherein the backing layer comprises a switchable material that increases in moisture vapour permeability when in contact with liquid.

16. A negative pressure wound therapy system, comprising:
- a wound dressing comprising:
  - a backing layer including a proximal, wound-facing face and a distal face;
  - a lower permeable layer configured to contact a wound;
  - a chamber between the backing layer and the lower permeable layer; and
  - a resiliently flexible filler positioned within the chamber, the resiliently flexible filler comprising an absorbent material configured to retain wound exudate within the chamber, and
- a fluid outlet conduit configured to provide fluid communication between a negative pressure source and the wound dressing, the fluid outlet conduit being in fluid communication with the chamber of the wound dressing;
- wherein the filler consists essentially of a cellulosic material configured to absorb the wound exudate within a cellulosic gel upon application of negative pressure to the wound dressing.

17. The system of claim 16, further comprising an upper permeable layer above the resiliently flexible filler and underneath the backing layer, the upper permeable layer at least partially containing the resiliently flexible filler.

18. The system of claim 17, further comprising a foam layer above the upper permeable layer and underneath the backing layer.

19. The system of claim 16, wherein the lower permeable layer is attached to the backing layer.

20. The system of claim 16, wherein the lower permeable layer, the resiliently flexible filler and the backing layer are integral with each other.

21. The system of claim 16, further comprising a connector attached to the backing layer and configured to connect the fluid outlet conduit to the wound dressing.

22. The system of claim 16, further comprising a negative pressure source configured to apply negative pressure to the wound dressing through the fluid outlet conduit.

23. The system of claim 11, further comprising a valve configured to be closed when the negative pressure source is disconnected.

24. The system of claim 22, further comprising a valve configured to be closed when the negative pressure source is disconnected.

* * * * *